(12) United States Patent
Cronenberg et al.

(10) Patent No.: US 10,357,614 B2
(45) Date of Patent: Jul. 23, 2019

(54) INJECTION PEN

(71) Applicant: Becton, Dickinson and Company, Franklin Lakes, NJ (US)

(72) Inventors: Richard Cronenberg, Mahwah, NJ (US); Michael V. Quinn, East Hanover, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 14/909,456

(22) PCT Filed: Jul. 30, 2014

(86) PCT No.: PCT/US2014/048911
§ 371 (c)(1),
(2) Date: Feb. 1, 2016

(87) PCT Pub. No.: WO2015/017550
PCT Pub. Date: Feb. 5, 2015

(65) Prior Publication Data
US 2016/0193422 A1 Jul. 7, 2016

Related U.S. Application Data

(60) Provisional application No. 61/861,918, filed on Aug. 2, 2013.

(51) Int. Cl.
*A61M 5/00* (2006.01)
*A61M 5/315* (2006.01)
(Continued)

(52) U.S. Cl.
CPC .......... *A61M 5/31543* (2013.01); *A61M 5/20* (2013.01); *A61M 5/31553* (2013.01);
(Continued)

(58) Field of Classification Search
CPC ...... A61M 5/20; A61M 5/24; A61M 5/31543; A61M 5/31553; A61M 5/31585;
(Continued)

(56) References Cited

U.S. PATENT DOCUMENTS 5,279,585 A * 1/1994 Balkwill ............. A61M 5/3158
604/211
5,279,858 A * 1/1994 Suzuki ...................... B41F 3/52
101/488

(Continued)

FOREIGN PATENT DOCUMENTS

CN 204219525 U 3/2015
WO WO-99/38554 A1 8/1999
(Continued)

*Primary Examiner* — Kevin C Sirmons
*Assistant Examiner* — Tezita Z Watts
(74) *Attorney, Agent, or Firm* — Dickinson Wright PLLC

(57) ABSTRACT

An injection pen (1) includes a housing (2), a lead screw (75), a dose set member (6), a setback member (17), and a rotatable driver (60). The lead screw (75) is axially moveable in the housing (2). The dose set member (6) is connected to the housing (2) for dose setting and dose correcting. The setback member (17) is operatively connected to the dose set member (6). The rotatable driver (60) is operatively connected to the setback member (17) and the lead screw (75). The driver (60) is prevented from rotating during dose setting and dose correcting, and the driver (60) rotates during an injection to axially move the lead screw (75).

23 Claims, 32 Drawing Sheets

(51) Int. Cl.
  *A61M 5/20* (2006.01)
  *A61M 5/24* (2006.01)
  *A61M 5/31* (2006.01)

(52) U.S. Cl.
  CPC .......... *A61M 5/31585* (2013.01); *A61M 5/24* (2013.01); *A61M 5/31551* (2013.01); *A61M 5/31561* (2013.01); *A61M 2005/2407* (2013.01); *A61M 2005/3126* (2013.01); *A61M 2205/581* (2013.01); *A61M 2205/6018* (2013.01)

(58) Field of Classification Search
  CPC .......... A61M 5/31551; A61M 5/31561; A61M 2005/2407; A61M 2005/3126; A61M 2205/581; A61M 2205/6018
  See application file for complete search history.

(56) References Cited

U.S. PATENT DOCUMENTS

| | | | |
|---|---|---|---|
| 5,383,865 A | 1/1995 | Michel | |
| 5,626,566 A | 5/1997 | Petersen et al. | |
| 5,674,204 A * | 10/1997 | Chanoch | A61M 5/31535 604/207 |
| 5,938,642 A | 8/1999 | Burroughs | |
| 6,235,004 B1 | 5/2001 | Steenfeldt-Jensen et al. | |
| 7,195,616 B2 | 3/2007 | Diller et al. | |
| 7,241,278 B2 * | 7/2007 | Moller | A61M 5/24 604/211 |
| 8,021,345 B2 | 9/2011 | Veasey et al. | |
| RE43,834 E | 11/2012 | Steenfeldt-Jensen et al. | |
| 2004/0267207 A1 * | 12/2004 | Veasey | A61M 5/31551 604/208 |
| 2006/0206057 A1 | 9/2006 | DeRuntz et al. | |
| 2008/0077095 A1 | 3/2008 | Kirchhofer | |
| 2009/0012479 A1 | 1/2009 | Moller et al. | |
| 2009/0264828 A1 | 10/2009 | Dette et al. | |
| 2009/0275916 A1 | 11/2009 | Harms et al. | |
| 2010/0114037 A1 | 5/2010 | Moser et al. | |
| 2010/0168677 A1 | 7/2010 | Gabriel et al. | |
| 2010/0324494 A1 | 12/2010 | Plumptre | |
| 2010/0324495 A1 | 12/2010 | Jones | |
| 2010/0324496 A1 | 12/2010 | Plumptre et al. | |
| 2010/0331788 A1 | 12/2010 | Plumptre et al. | |
| 2011/0130723 A1 | 6/2011 | Hirschel et al. | |
| 2011/0276006 A1 | 11/2011 | Matthias et al. | |
| 2011/0276009 A1 | 11/2011 | Veasey | |
| 2011/0301550 A1 | 12/2011 | Veasey et al. | |
| 2011/0319835 A1 * | 12/2011 | Burren | A61M 5/31541 604/207 |
| 2012/0041386 A1 | 2/2012 | Veasey | |
| 2012/0046643 A1 | 2/2012 | Plumptre et al. | |
| 2012/0089100 A1 | 4/2012 | Veasey | |
| 2012/0095413 A1 | 4/2012 | Nzike | |
| 2012/0143146 A1 | 6/2012 | Strehl et al. | |
| 2012/0157929 A1 | 6/2012 | Plumptre | |
| 2012/0165743 A1 | 6/2012 | Jones | |
| 2012/0165744 A1 | 6/2012 | Jones | |
| 2012/0172809 A1 | 7/2012 | Plumptre | |
| 2012/0172814 A1 | 7/2012 | Plumptre | |
| 2012/0209210 A1 | 8/2012 | Plumptre et al. | |
| 2012/0209211 A1 | 8/2012 | Plumptre | |
| 2012/0209212 A1 | 8/2012 | Plumptre et al. | |
| 2012/0215176 A1 | 8/2012 | Veasey et al. | |
| 2012/0245532 A1 * | 9/2012 | Frantz | A61M 5/31551 604/211 |
| 2012/0265151 A1 | 10/2012 | Nzike et al. | |
| 2012/0265153 A1 | 10/2012 | Jugl et al. | |
| 2012/0277683 A1 | 11/2012 | Møller | |
| 2012/0283647 A1 | 11/2012 | Cronenberg et al. | |
| 2012/0283659 A1 | 11/2012 | Kouyoumjian | |
| 2012/0289908 A1 | 11/2012 | Kouyoumjian et al. | |

FOREIGN PATENT DOCUMENTS

| | | | |
|---|---|---|---|
| WO | WO-2006/058883 A2 | 6/2006 | |
| WO | 2011068531 A1 | 6/2011 | |
| WO | WO 2011068531 A1 * | 6/2011 | ........ A61M 5/31535 |
| WO | WO-2011068531 A1 * | 6/2011 | ........ A61M 5/31535 |
| WO | 2012017036 A1 | 2/2012 | |
| WO | 2012125876 A1 | 9/2012 | |
| WO | 2013137893 A1 | 9/2013 | |

\* cited by examiner

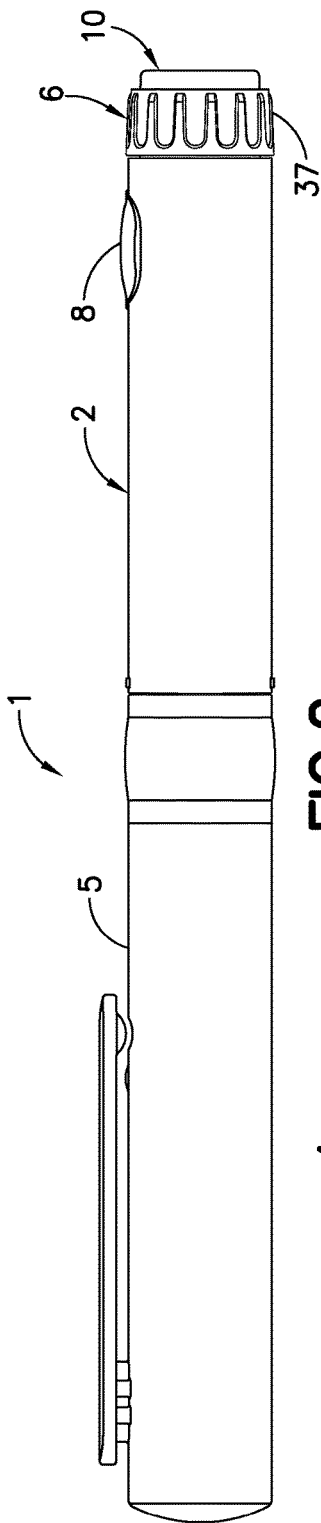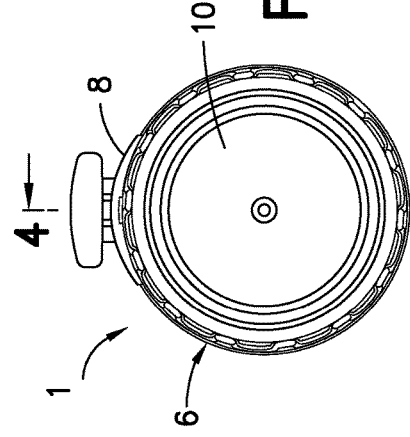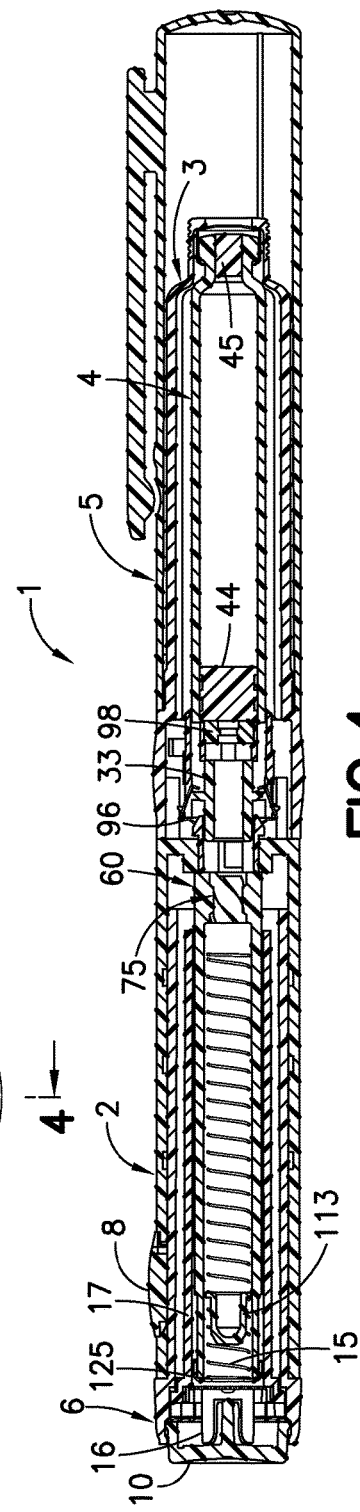

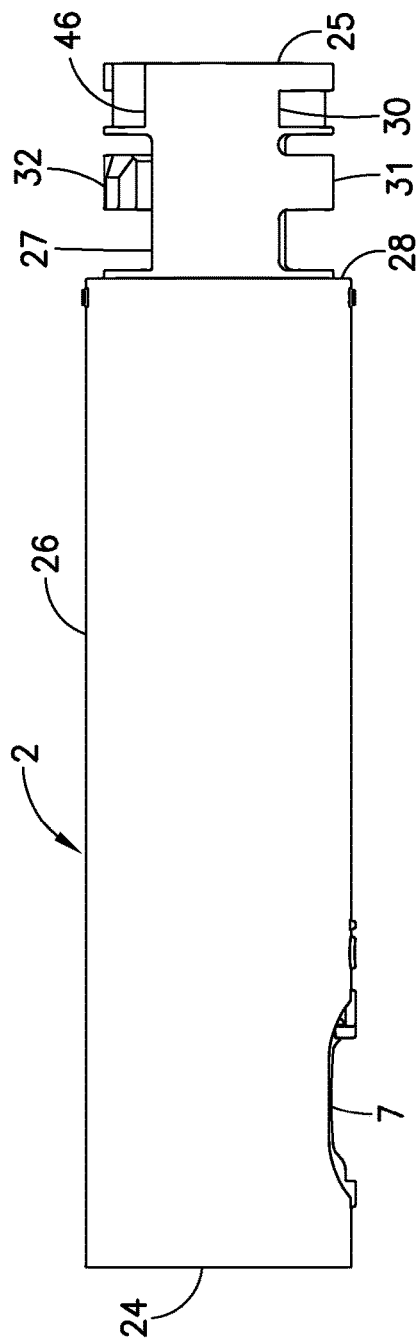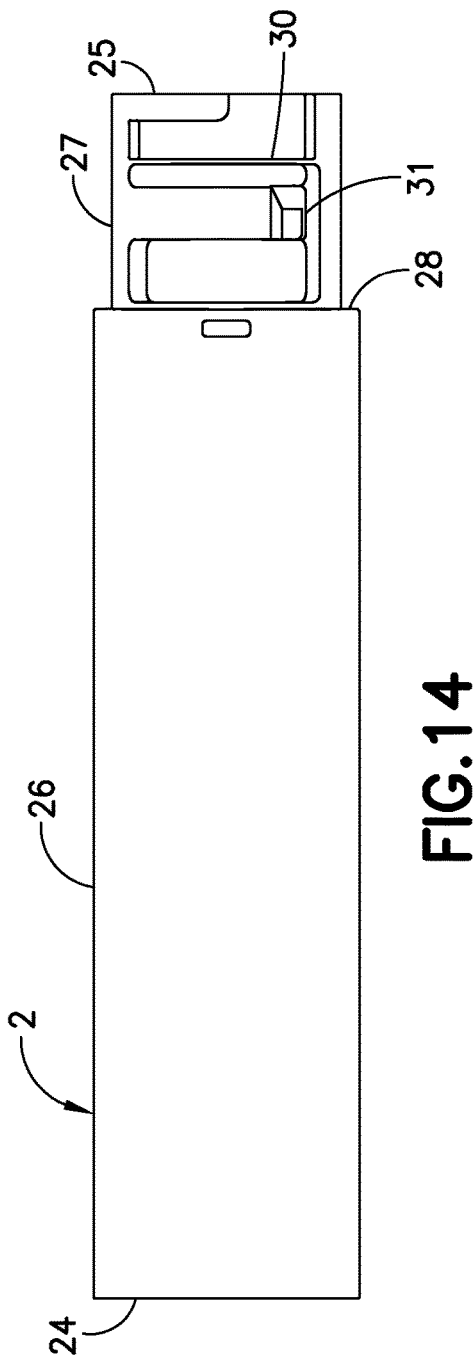

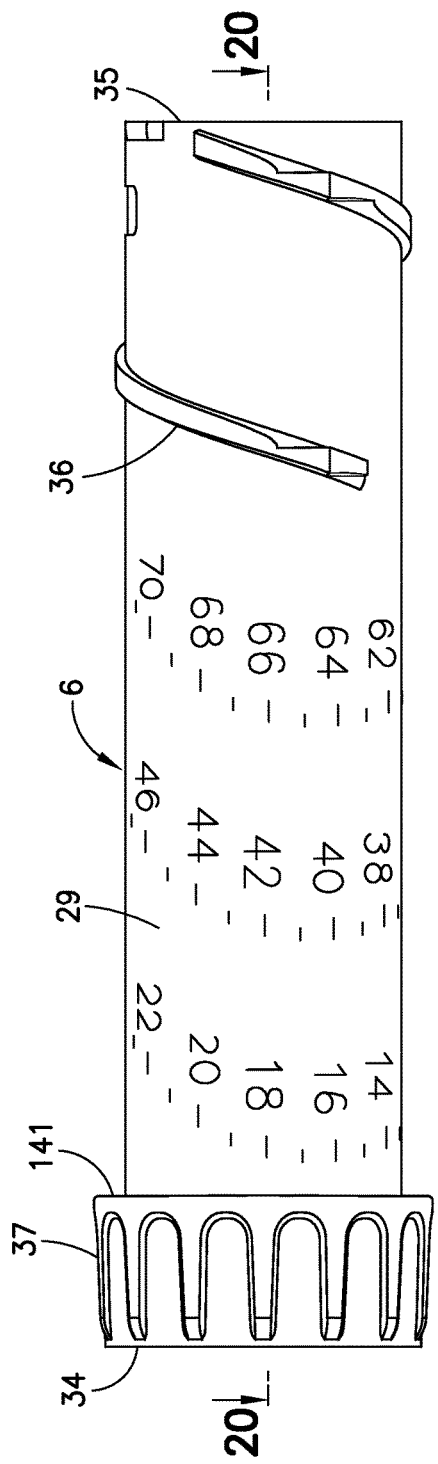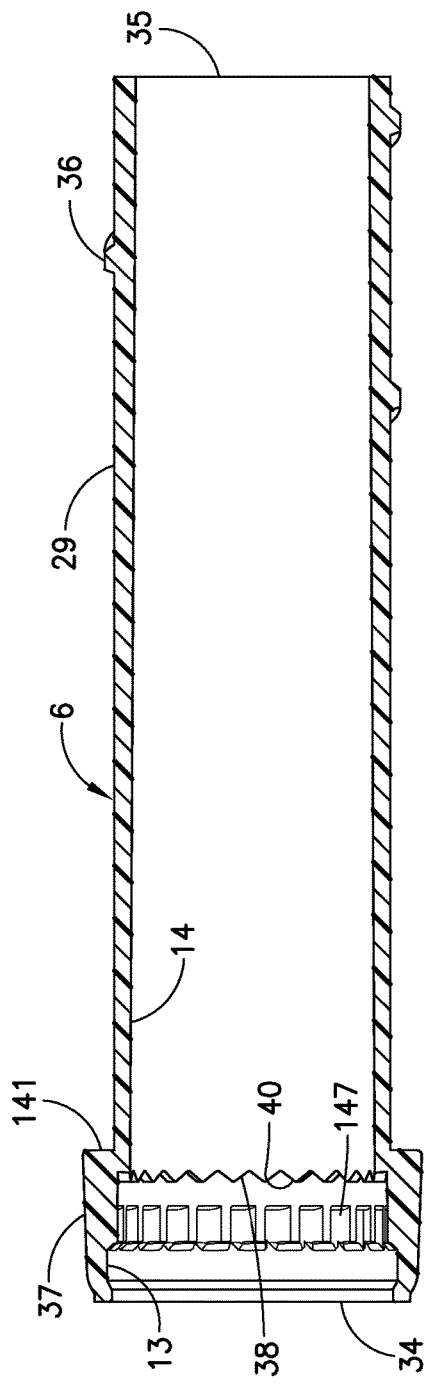

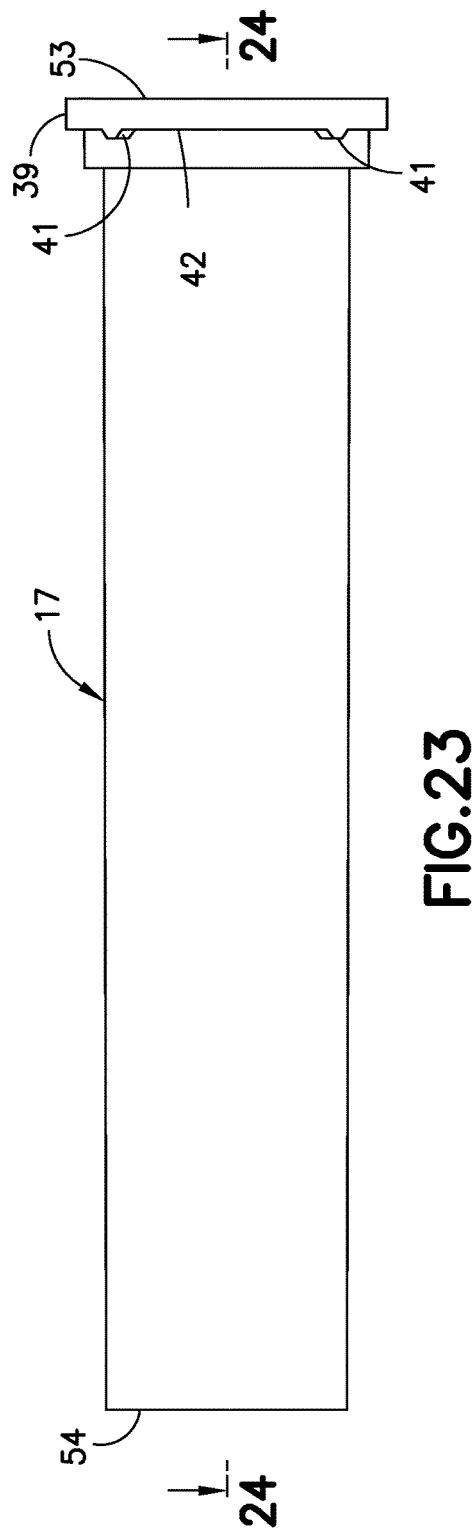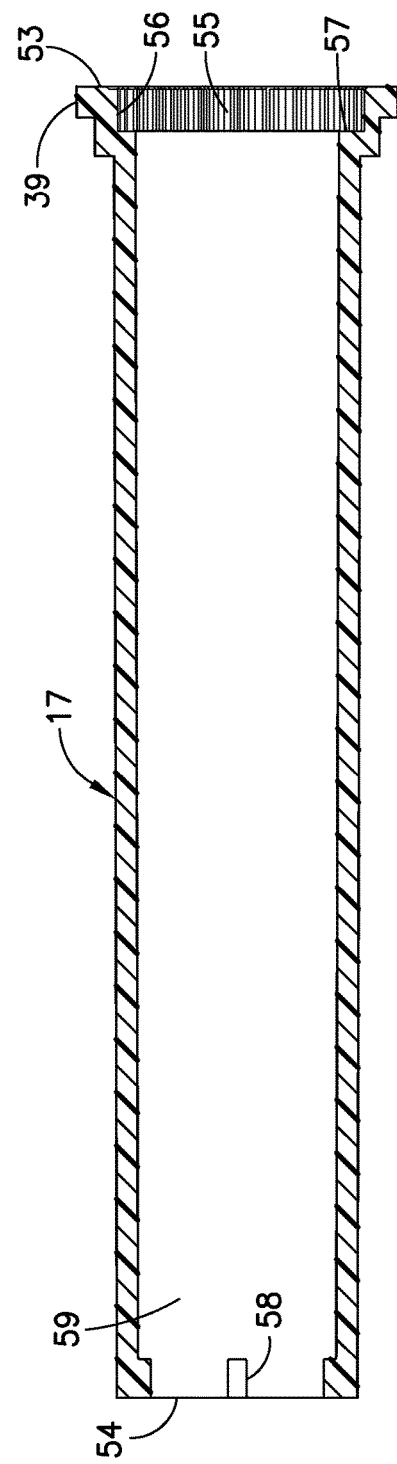
FIG.23
FIG.24

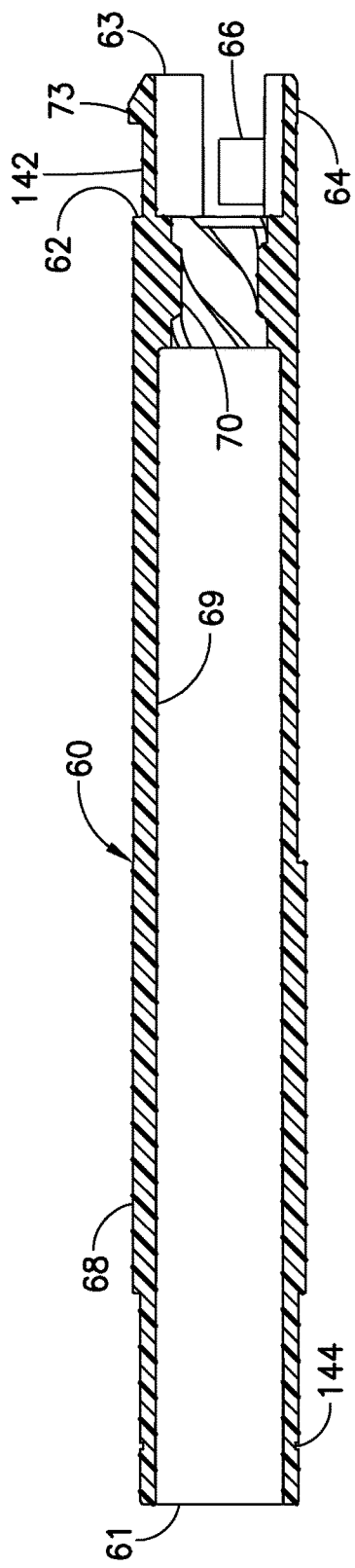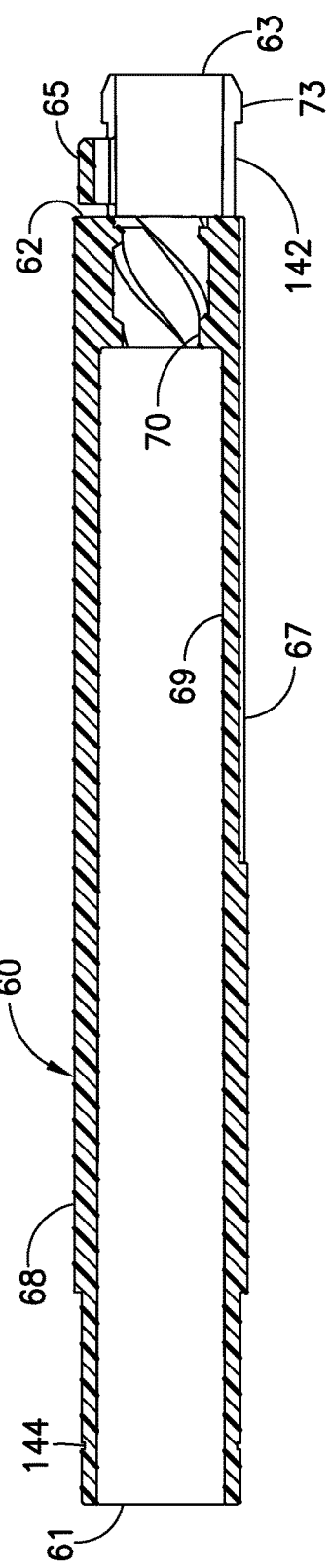

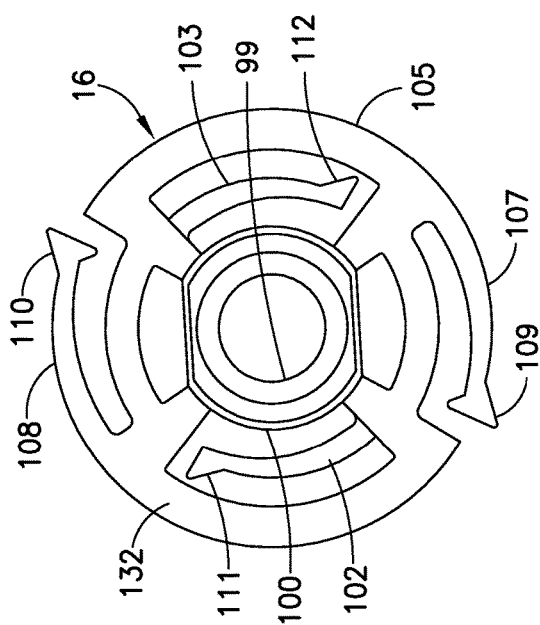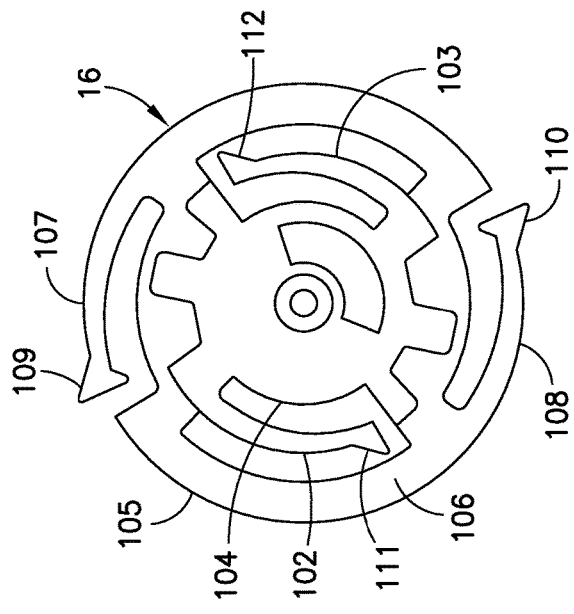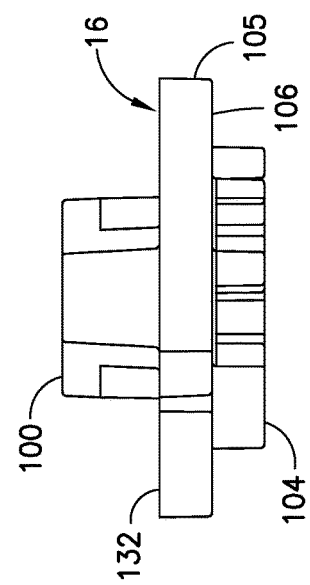

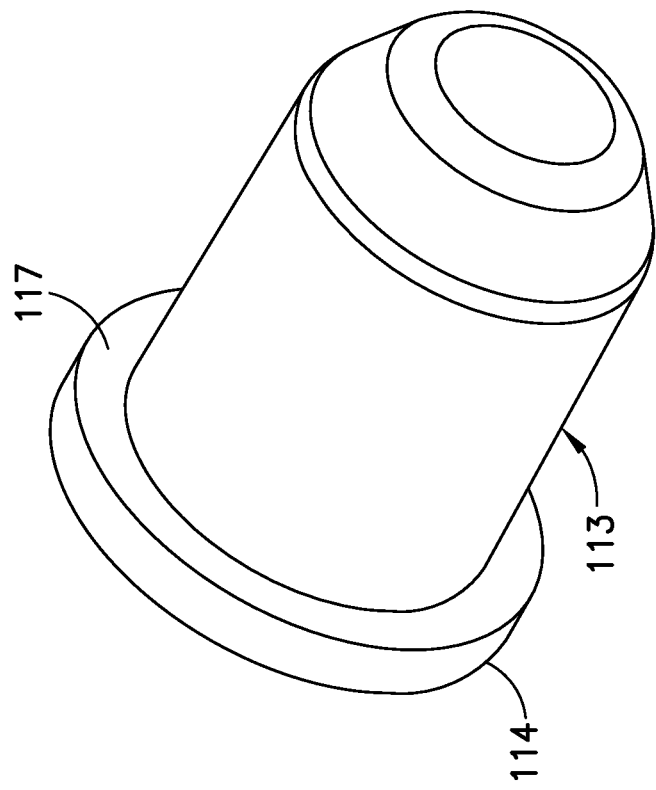
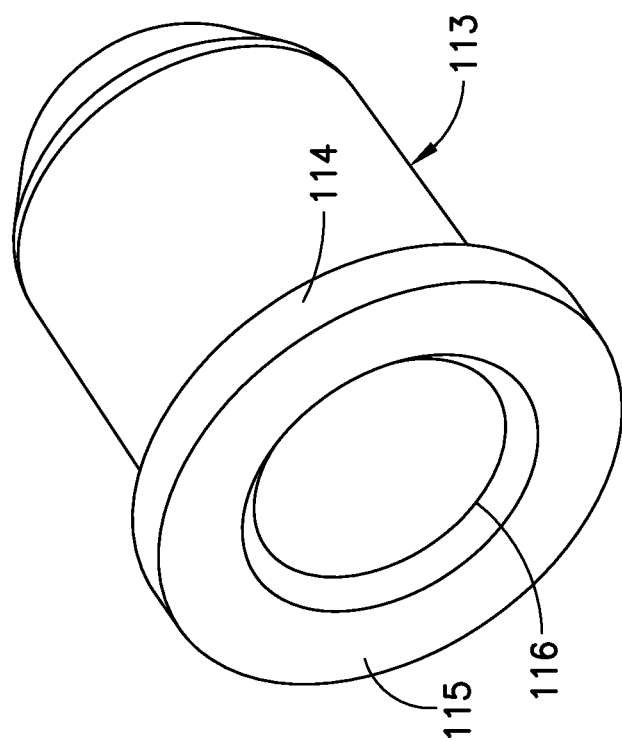
FIG. 44
FIG. 45

INJECTION PEN

RELATED APPLICATIONS

This application claims the benefit of U.S. Provisional Patent Application Ser. No. 61/861,918, filed on Aug. 2, 2013, which is hereby incorporated by reference in its entirety.

FIELD OF THE INVENTION

The present invention relates generally to a pen-type medical injection device. More particularly, the present invention relates to a reusable pen-type medical injection device. Still more particularly, the present invention relates to a reusable pen-type medical injection device in which an incorrect dose setting can be corrected.

BACKGROUND OF THE INVENTION

In certain circumstances, it is desirable to inject medication directly into human tissue. Typically, syringes are used to inject selected doses of medicaments into a patient. Hypodermic syringe includes a syringe barrel having opposed proximal and distal ends. A cylindrical chamber wall extends between the ends and defines a fluid receiving chamber. The proximal end of the syringe barrel is substantially open and receives a plunger in sliding fluid tight engagement. The distal end of the syringe barrel includes a passage communicating with the chamber. A needle cannula may be mounted to the distal end of the syringe barrel, such that the lumen of the needle cannula communicates with the passage and the chamber of the syringe barrel. Movement of the plunger in a proximal direction draws fluid through the lumen of the needle cannula and into the chamber. Movement of the plunger in a proximal-to-distal direction urges fluid from the chamber and through the lumen of the needle cannula.

Medication to be injected with the prior hypodermic syringe often is stored in a vial having a pierceable elastomeric seal. Medication in the vial is accessed by piercing the elastomeric seal with the needle cannula. A selected dose of the medication may be drawn into the chamber of the syringe barrel by moving the plunger a selected distance in a proximal direction. The needle cannula may be withdrawn from the vial, and the medication may be injected into a patient by moving the plunger in a distal direction.

Some medication, such as insulin is self-administered. The typical diabetes patient will require injections of insulin several times during the course of a week or day. The required dose of insulin will vary from patient to patient, and for each patient may vary during the course of the day and from day to day. Usually, each diabetes patient will establish a regimen that is appropriate for his or her own medical condition and for his or her lifestyle. The regimen typically includes some combination of a slow or medium acting insulin and a faster acting insulin. Each of these regimens may require the diabetes patient to periodically self-administer insulin in public locations, such as places of employment or restaurants. The required manipulation of the standard hypodermic syringe and vial can be inconvenient and embarrassing in these public environments.

Medication delivery pens have been developed to facilitate the self-administration of medication. An example of one such medication delivery pen is described in U.S. Pat. No. 5,279,585 (Balkwill), which includes a vial holder into which a vial of insulin or other medication may be received.

There remains a need for a medication delivery pen that allows a user to easily set and correct a dosage prior to delivery.

SUMMARY OF EMBODIMENTS OF THE INVENTION

Exemplary embodiments of the present invention address at least the above problems and/or disadvantages and provide at least the advantages described below.

In accordance with an exemplary embodiment an injection pen includes a housing, a lead screw, a dose set member, a setback member, and a rotatable driver. The lead screw is axially moveable in the housing. The dose set member is connected to the housing for dose setting and dose correcting. The setback member is operatively connected to the dose set member. The rotatable driver is operatively connected to the setback member and the lead screw. The driver is prevented from rotating during dose setting and dose correcting, and the driver rotates during an injection to axially move the lead screw.

In accordance with an exemplary embodiment an injection pen includes a housing, a lead screw, a dose set member, a setback member, and a push button. The lead screw is axially moveable in the housing. The dose set member is connected to the housing for dose setting and dose correcting and includes a first mating feature. The setback member has a second mating feature for engaging the first mating feature. The push button is operatively connected setback member to cause the second mating feature to engage the first mating feature during an injection. The first mating feature is disengaged from the second mating feature during dose setting and dose correcting, and engaged with the second mating feature during an injection.

In accordance with an exemplary embodiment an injection pen includes a housing, a lead screw, a dose set member, a setback member, a clicker, and a rotatable driver. The lead screw is axially moveable in the housing. The dose set member is connected to the housing for dose setting and dose correcting. The setback member is operatively connected to the dose set member. The clicker is operatively coupled to the dose set member and the setback member. The rotatable driver is operatively connected to the setback member and the lead screw. The driver is prevented from rotating during dose setting and dose correcting, and the driver rotates during an injection to axially move the lead screw.

Additional objects, advantages and salient features of exemplary embodiments of the invention will become apparent to those skilled in the art from the following detailed description, which, taken in conjunction with annexed drawings, discloses exemplary embodiments of the invention.

BRIEF DESCRIPTION OF THE DRAWINGS

The above and other exemplary features and advantages of certain exemplary embodiments of the present invention will become more apparent from the following description of certain exemplary embodiments thereof when taken in conjunction with the accompanying drawings in which:

FIG. 2 is a side elevational view of the injection pen of FIG. 1;

FIG. 3 is a front elevational view of the injection pen of FIG. 1;

FIG. 4 is a side elevational view in cross-section of the injection pen taken along line 4-4 of FIG. 3;

FIG. 13 is a top plan view of the body of FIG. 12;

FIG. 14 is a side elevational view of the body of FIG. 12;

FIG. 19 is an elevational view of the dose set member of FIG. 17;

FIG. 20 is an elevational view in cross-section taken along the line 20-20 of the dose set member of FIG. 19;

FIG. 23 is an elevational view of the setback member of FIG. 21;

FIG. 24 is an elevational view in cross-section of the setback member taken along line 24-24 of FIG. 23;

FIG. 27 is a side elevational view in cross-section of the driver taken along line 27-27 of FIG. 26;

FIG. 28 is a top plan view in cross-section of the driver taken along line 28-28 of FIG. 26;

FIG. 41 is a bottom plan view of the clicker body of FIG. 39;

FIG. 42 is a top plan view of the clicker body of FIG. 39;

FIG. 43 is a side elevational view of the clicker body of FIG. 39;

FIG. 44 is a perspective view of a proximal end of a pilot cap of the injection pen of FIG. 7;

FIG. 45 is a perspective view of a distal end of the pilot cap of FIG. 44;

Throughout the drawings, like reference numerals will be understood to refer to like elements, features and structures.

DETAILED DESCRIPTION OF EXEMPLARY EMBODIMENT

The matters exemplified in this description are provided to assist in a comprehensive understanding of an exemplary embodiment of the invention with reference to the accompanying drawing figures. Accordingly, those of ordinary skill in the art will recognize that various changes and modifications of the exemplary embodiment described herein can be made without departing from the scope and spirit of the claimed invention. Also, descriptions of well-known functions and constructions are omitted for clarity and conciseness.

Figure 1:
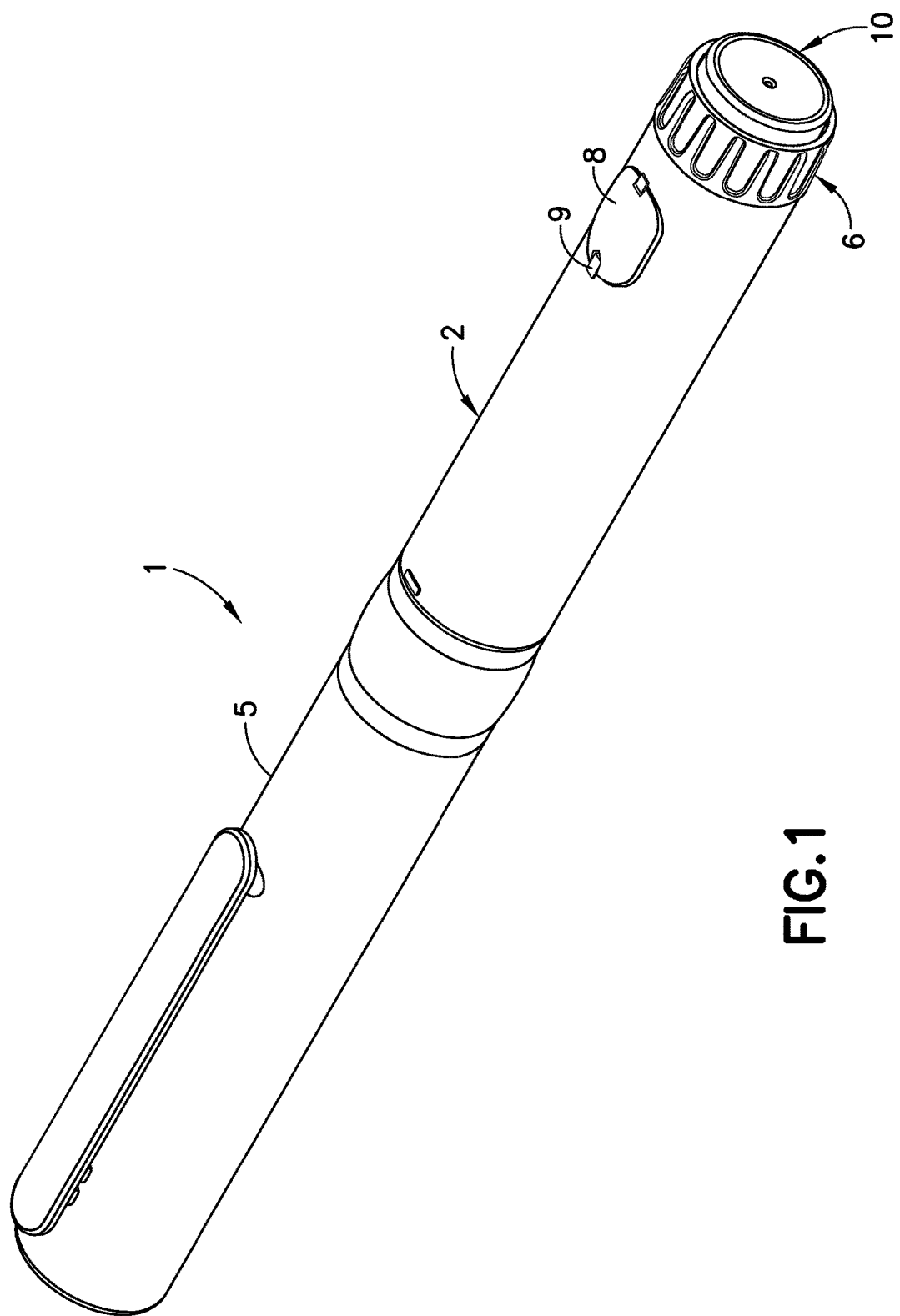
FIG. 1 is a perspective view of a medical injection pen in accordance with an exemplary embodiment of the present invention.
Figure 5:
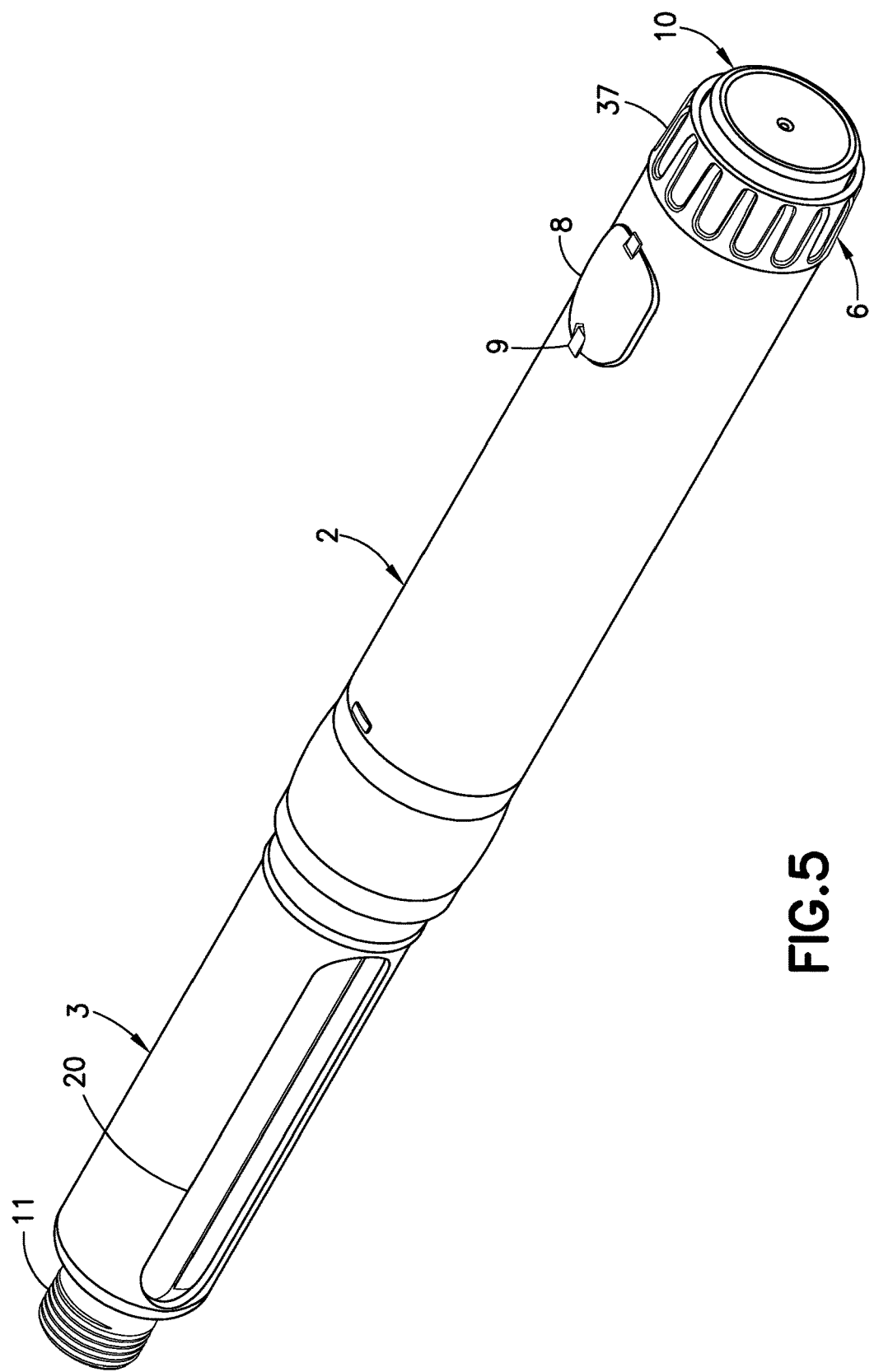
FIG. 5 is a perspective view of the injection pen of FIG. 1 with a cap removed.
Figure 6:
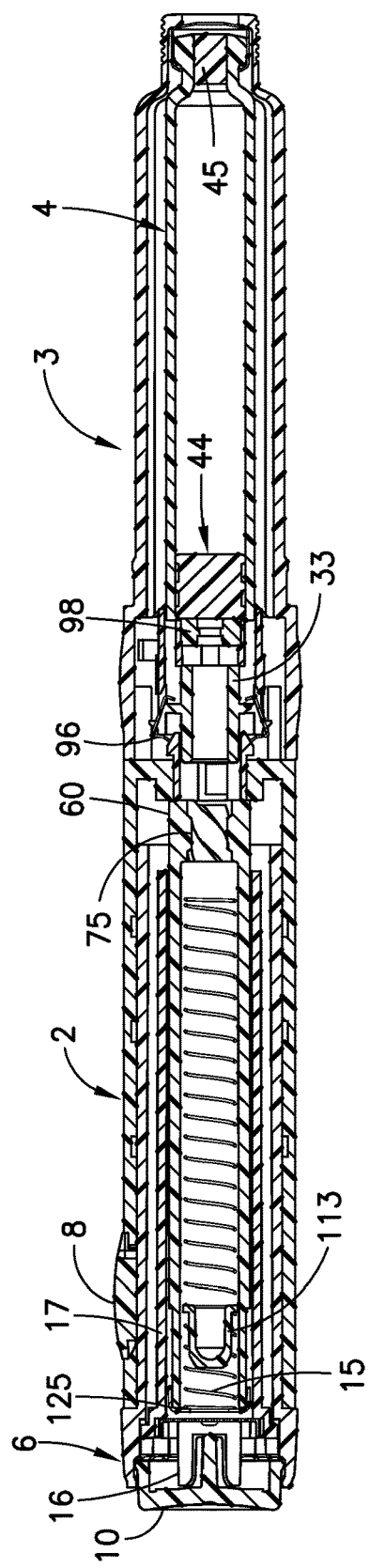
FIG. 6 is a side elevational view in cross-section of the injection pen of FIG. 5.

A medical injection pen 1 according to an exemplary embodiment is shown in FIGS. 1-7. The injection pen 1 includes a pen upper body 2 or housing 2, which houses a plurality of dose setting and injection components. The pen upper body 2 is connected to a vial retainer or cartridge holder 3, which houses a medication cartridge 4, as shown in FIGS. 4 and 6. The injection pen 1 may also include a lower pen cap 5 to cover the cartridge 4 and cartridge holder 3 when the injection pen 1 is not in use. A conventional pen needle 151 can be connected to a threaded portion 11 of the cartridge holder 3. An outer shield 152 can cover a needle of an attached pen needle to prevent accidental needle sticks upon removal of the lower pen cap 5.

The injection pen 1 includes a dose set member 6 having a knob portion 37 that is rotated by a user to set a desired dose. The dose set member 6 also includes a plurality of numerals corresponding to a number of dosage units that are visible through a window 7 and lens 8 provided in the pen upper body 2. A user rotates the dose set member 6 until the desired dose is visible in the lens 8. The pen upper body 2 may include an arrow or other indicator 9 to precisely indicate the set dose. Once the desired dose is set, a user presses the button 10 until the set dosage amount is completely injected.

FIGS. 4 and 6 depict a cross-section of the injection pen 1 in accordance with an exemplary embodiment of the present invention. Reference to the individual components may be better understood in view of the exploded assembly view shown in FIG. 7. As shown, the push button 10 is provided at a proximal end, closest to a user and farthest from the pen needle 151 connected to the cartridge holder 3. The push button 10 includes an annular bead or rim 12 that engages with a corresponding annular groove 13 provided on an internal surface 14 of the dose set member 6. In an exemplary embodiment, the annular rim 12 and groove 13 connection is a friction fit that maintains the push button 10 in a biased position on the dose set member 6 under the force of a spring member 15, but allows the push button 10 to be pushed into the dose set member 6 for injecting a set dose. The interior of the push button 10 accommodates a clicker body 16 that rests on an internal surface at a proximal end of a setback member 17. The push button 10 is designed to rotate freely on the clicker body 16.

Figure 8:
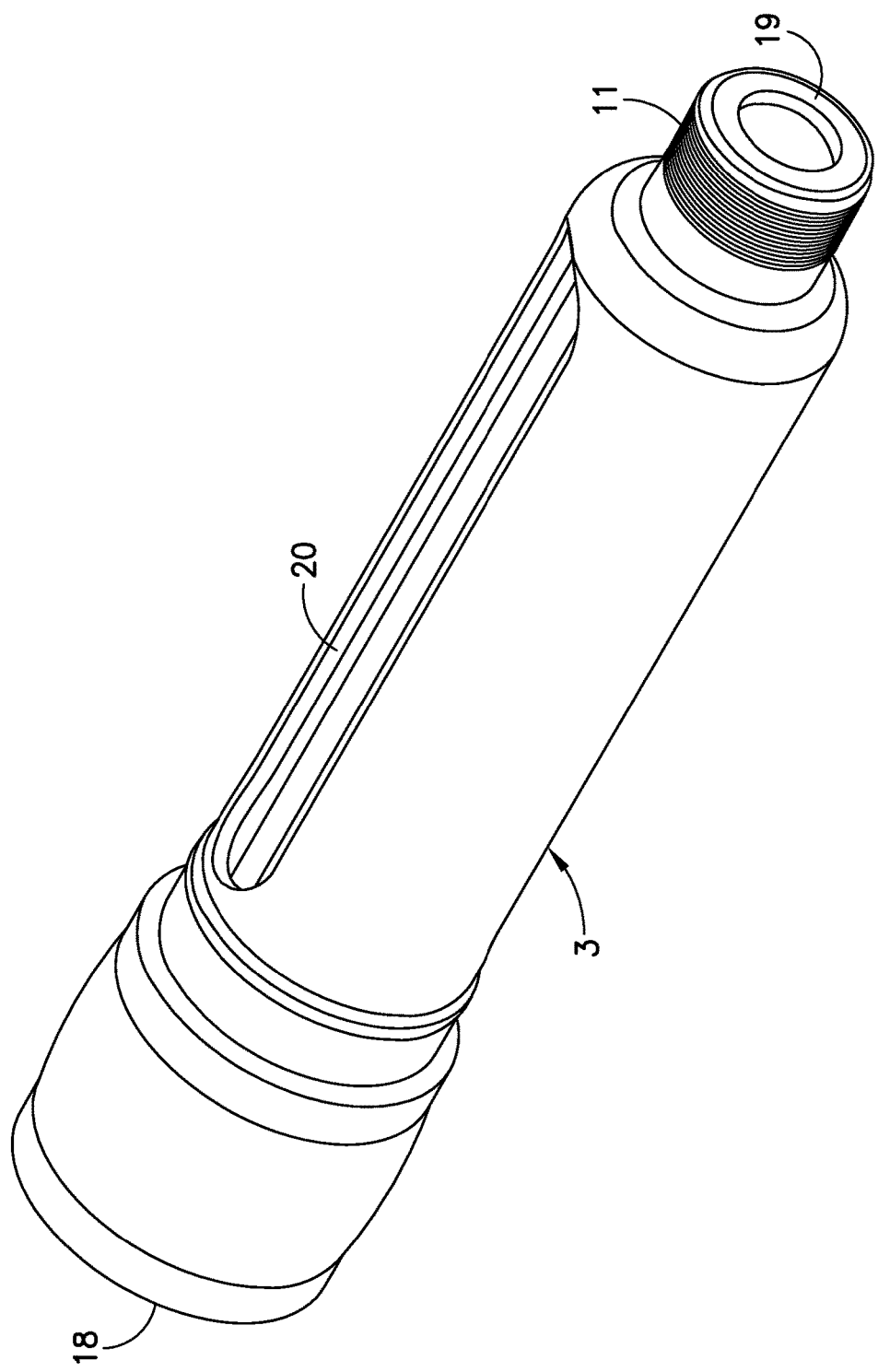
FIG. 8 is a perspective view of a cartridge holder of the injection pen of FIG. 7.
Figure 9:
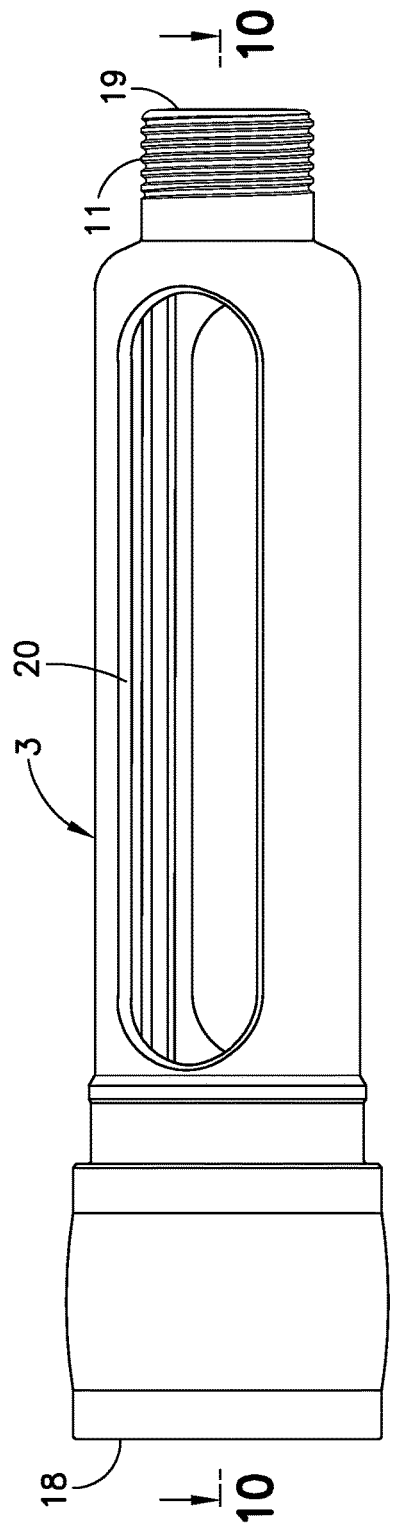
FIG. 9 is a side elevational view of the cartridge holder of FIG. 8.
Figure 10:
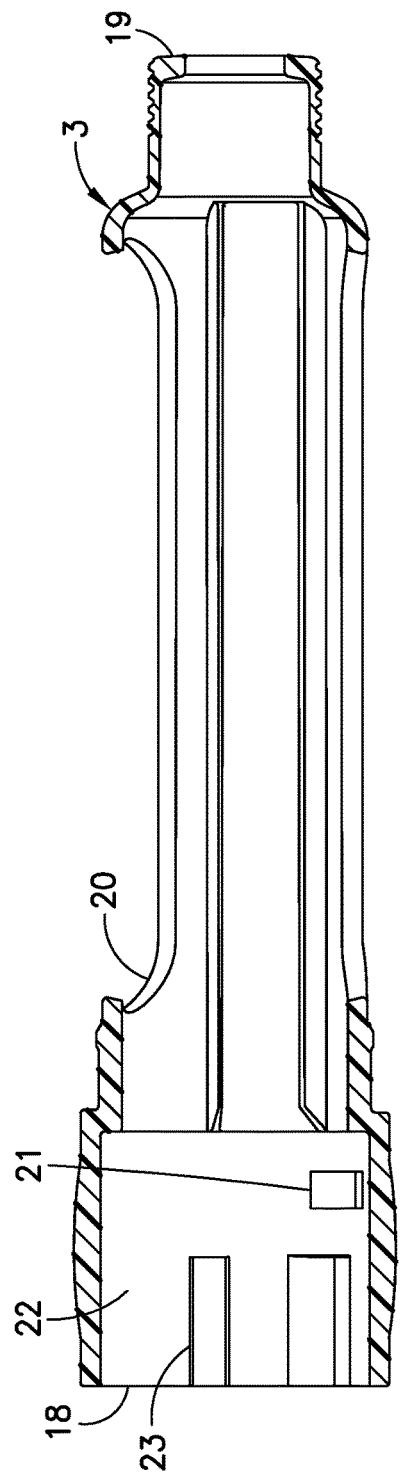
FIG. 10 is a side elevational view in cross-section taken along line 10-10 of FIG. 9.

According to an exemplary embodiment, a cartridge holder 3 is a substantially hollow member having an open first end 18 and an open second end 19, as best shown in FIGS. 8-10. A cartridge 4 is inserted through the opening at the first end 18 of the cartridge holder 3. A threaded portion 11 extends from the second end 19 toward the first end 18 of the cartridge holder 3 to receive a standard pen needle 151. A window 20 is disposed in the cartridge holder 3 such that the cartridge 4 is visible therethrough, allowing a user to view the volume of medicament in the cartridge 4. A tab 21 is formed on an inner surface 22 of the cartridge holder 3, spaced inwardly from the first end 18, as shown in FIG. 10. The tab 21 is adapted to engage with a corresponding groove 30 on the body 2. A protrusion 23 extends axially along the inner surface 22 of the cartridge holder at the first end 18.

Figure 7:
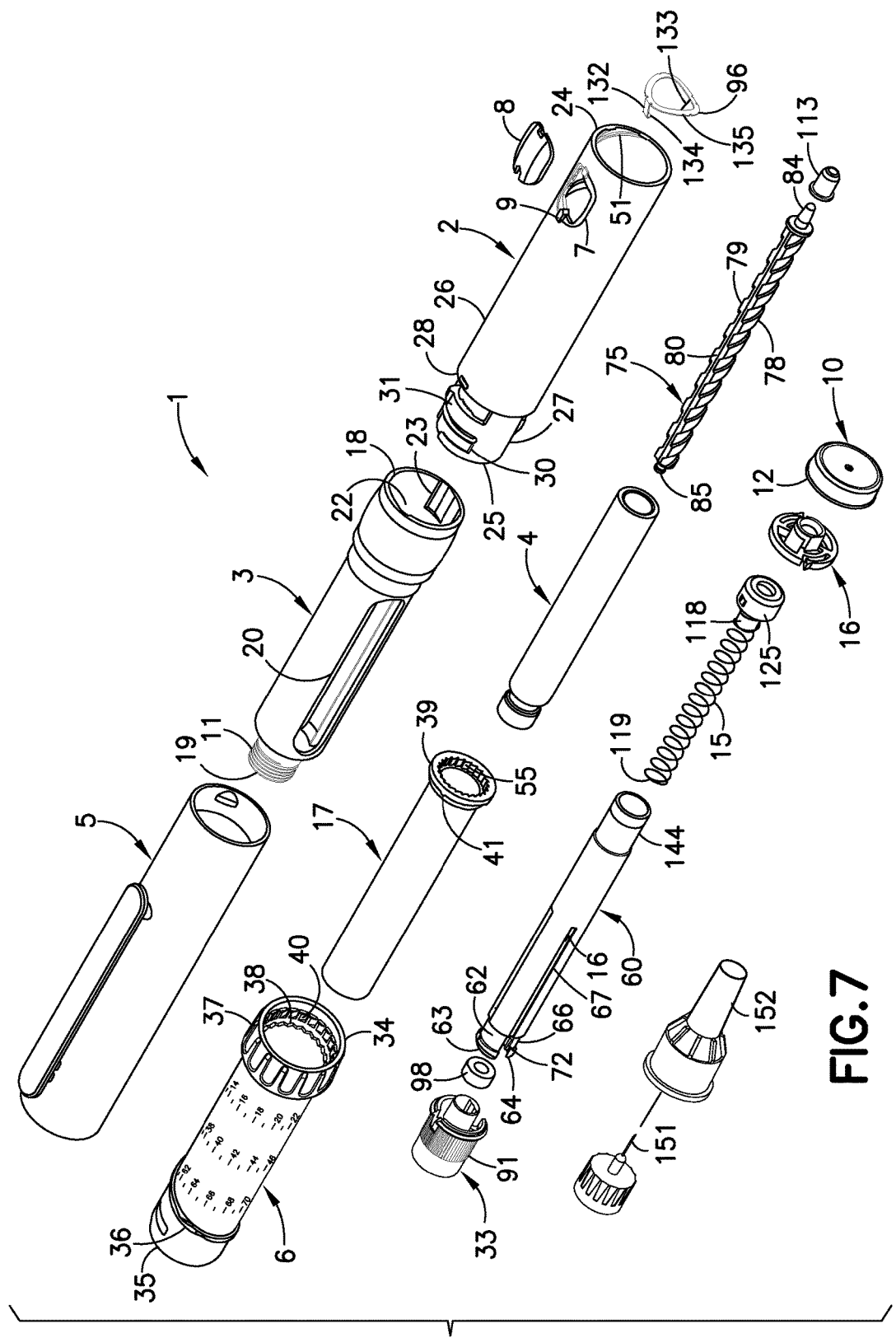
FIG. 7 is an exploded assembly view of the injection pen of FIG. 1.
Figure 11:
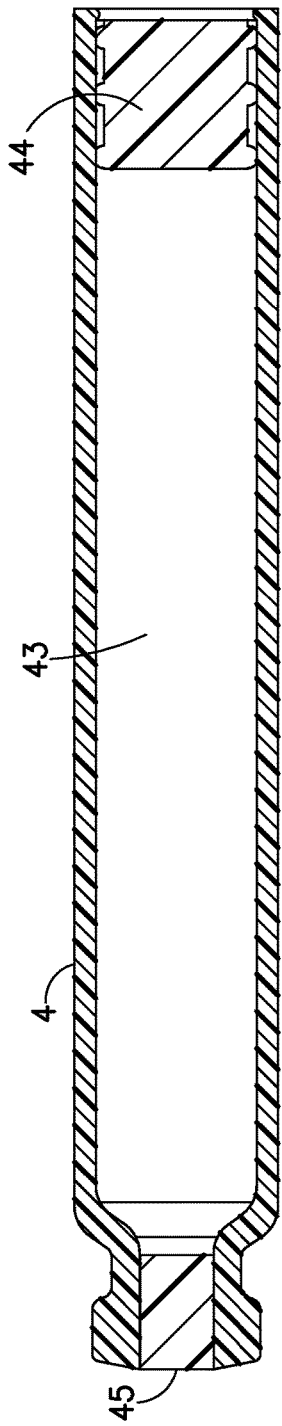
FIG. 11 is an elevational view in cross-section of a cartridge of the injection pen of FIG. 7.
Figure 12:
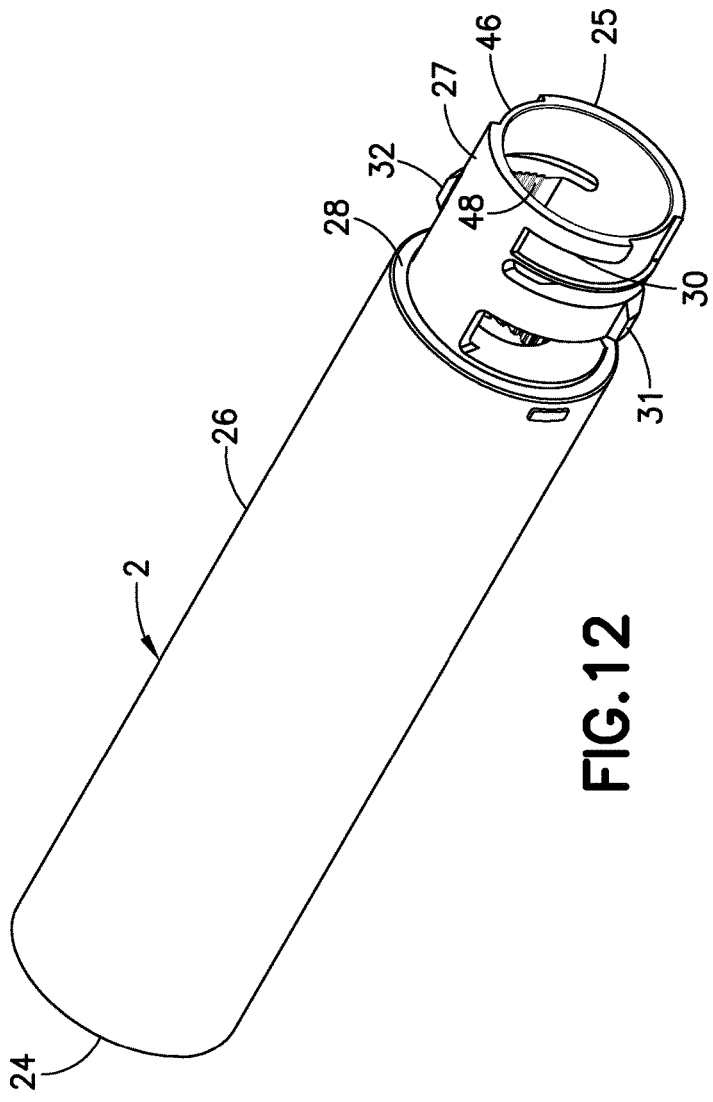
FIG. 12 is a perspective view of a body of the injection pen of FIG. 7.
Figure 15:
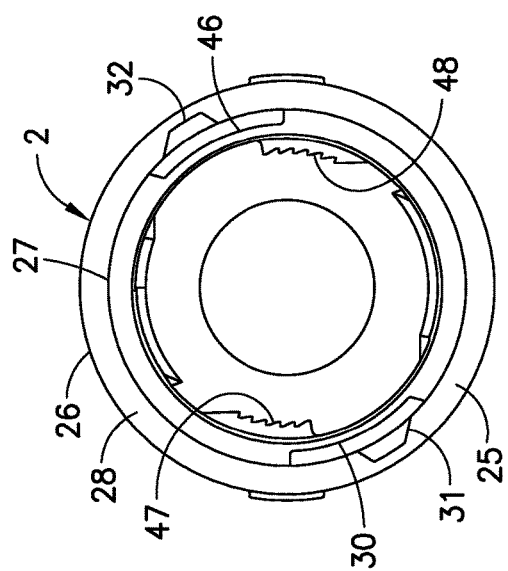
FIG. 15 is a front elevational view of the body of FIG. 12.

According to an exemplary embodiment, the cartridge 4, as best shown in FIGS. 7 and 11, includes an inner cavity 43 between a stopper 44 and a septum 45 for storing a medicament. The stopper 44 and the septum 45 seal the cartridge 4. The stopper 44 is axially movable in the cavity to administer the medicament. A standard pen needle 151 pierces the septum 45 when the pen needle is connected to the cartridge holder 3, thereby creating a flow path out of the cartridge 4 when the stopper 44 is moved through the cartridge 4 by the lead screw 75.

According to an exemplary embodiment shown in FIGS. 12-16, the upper body 2 is a substantially tubular member having a first end 24 and a second end 25. A first portion 26 of the upper body 2 extends from the first end 24 toward the second end 25. A second portion 27 of the upper body 2 extends from the second end 25 toward the first end 24. A shoulder 28 is formed at the intersection of the first and second portions 26, 27. The window 7 is disposed in the first portion 26 of the upper body 2 such that an outer surface 29 of the dose set member 6 is visible therethrough. In various exemplary embodiments, an indicator 9 is disposed on a side of the window to facilitate viewing the dose setting numbers on the outer surface 29 of the dose set member 6.

The second portion 27 of the upper body 2 includes a groove 30 that has an opening adjacent the second end 25. The groove 30 receives the tab 21 of the cartridge holder 3, thereby forming a bayonet connection to secure the cartridge holder to the upper body 2. In various exemplary embodiments, the groove 30 is substantially L-shaped with a first leg adjacent the opening to receive the cartridge holder tab 21, and a second leg substantially perpendicular to the first leg to abut or retain the cartridge holder tab 21. In certain embodiments, a substantially similar second groove 46 is disposed diametrically opposite the groove 30 to facilitate securing the cartridge holder 3 to the upper body 2. Alternatively, threads can be formed in the second portion 27 of the upper body 2 at the second end 25 instead of the groove 30 to threadably receive the cartridge holder 3.

Figure 16:
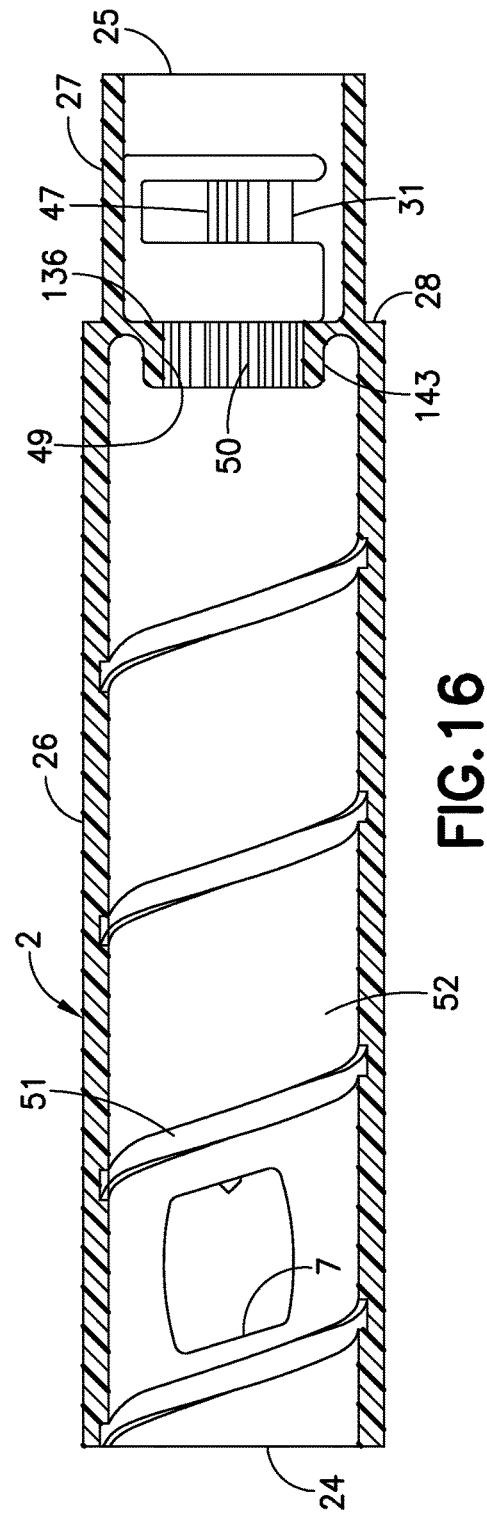
FIG. 16 is side elevational view in cross-section of the body of FIG. 13.
Figure 17:
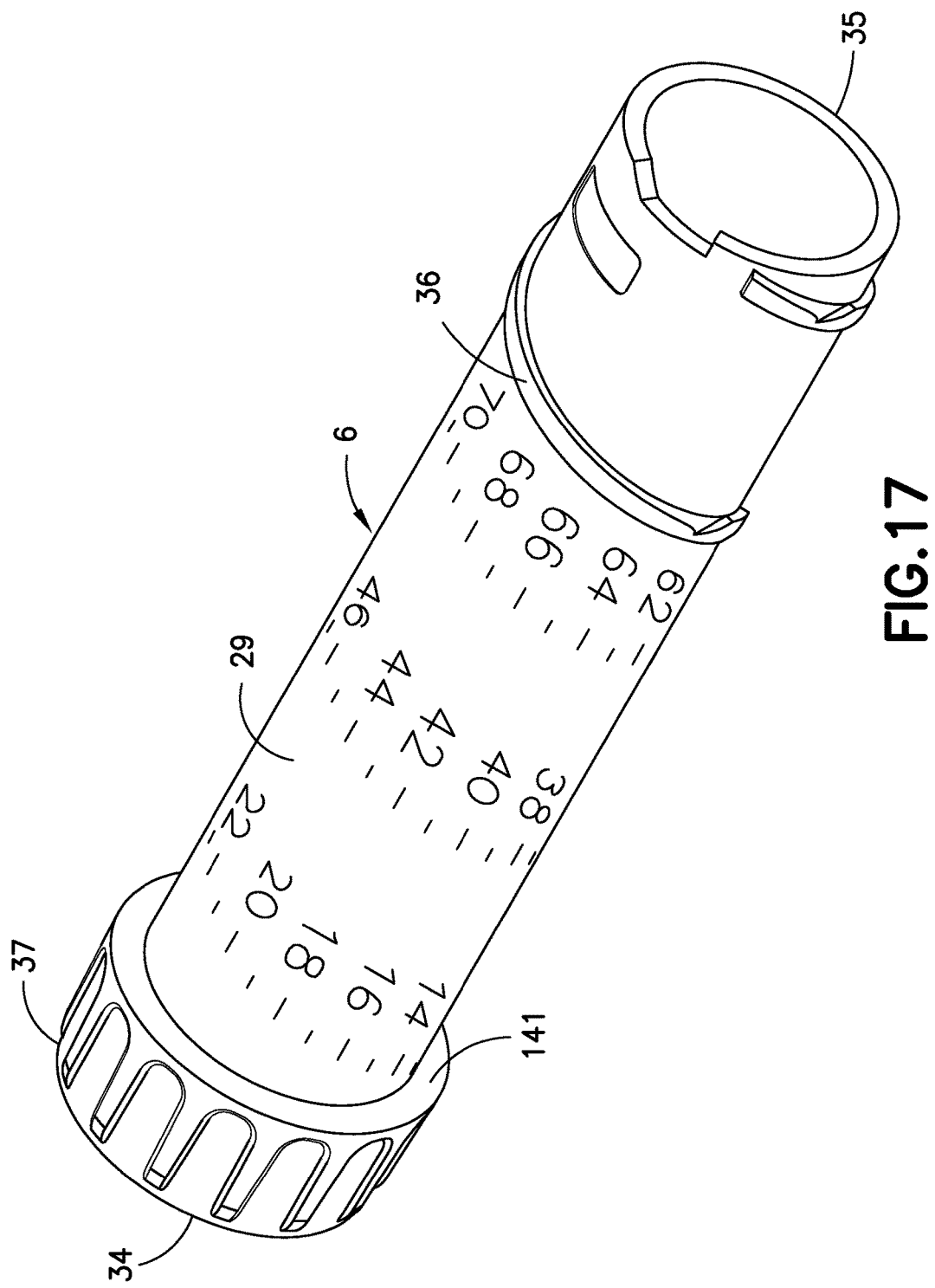
FIG. 17 is a perspective view of a proximal end of a dose set member of the injection pen of FIG. 7.
Figure 18:
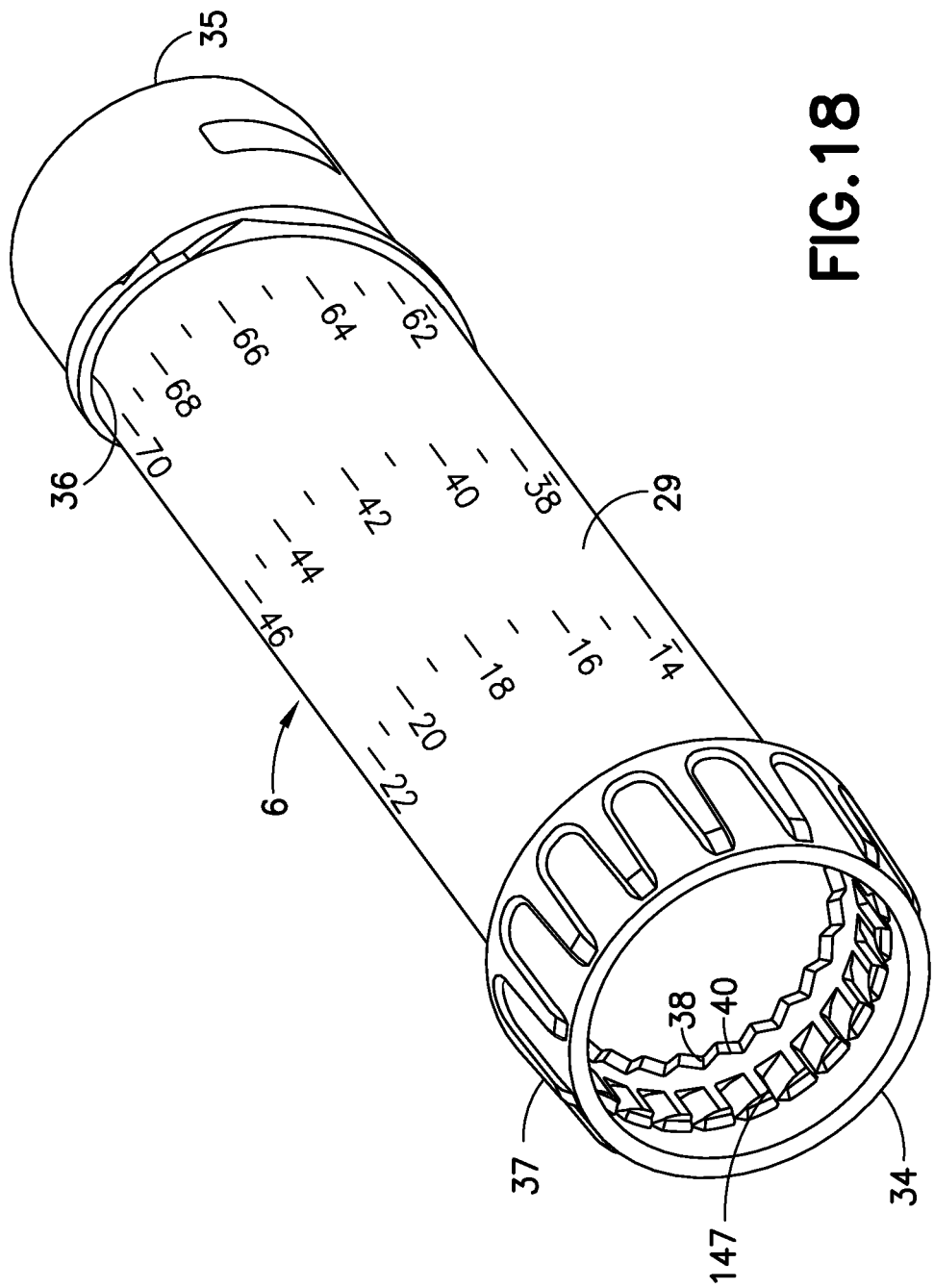
FIG. 18 is a perspective view of a distal end of the dose set member of FIG. 17.
Figure 21:
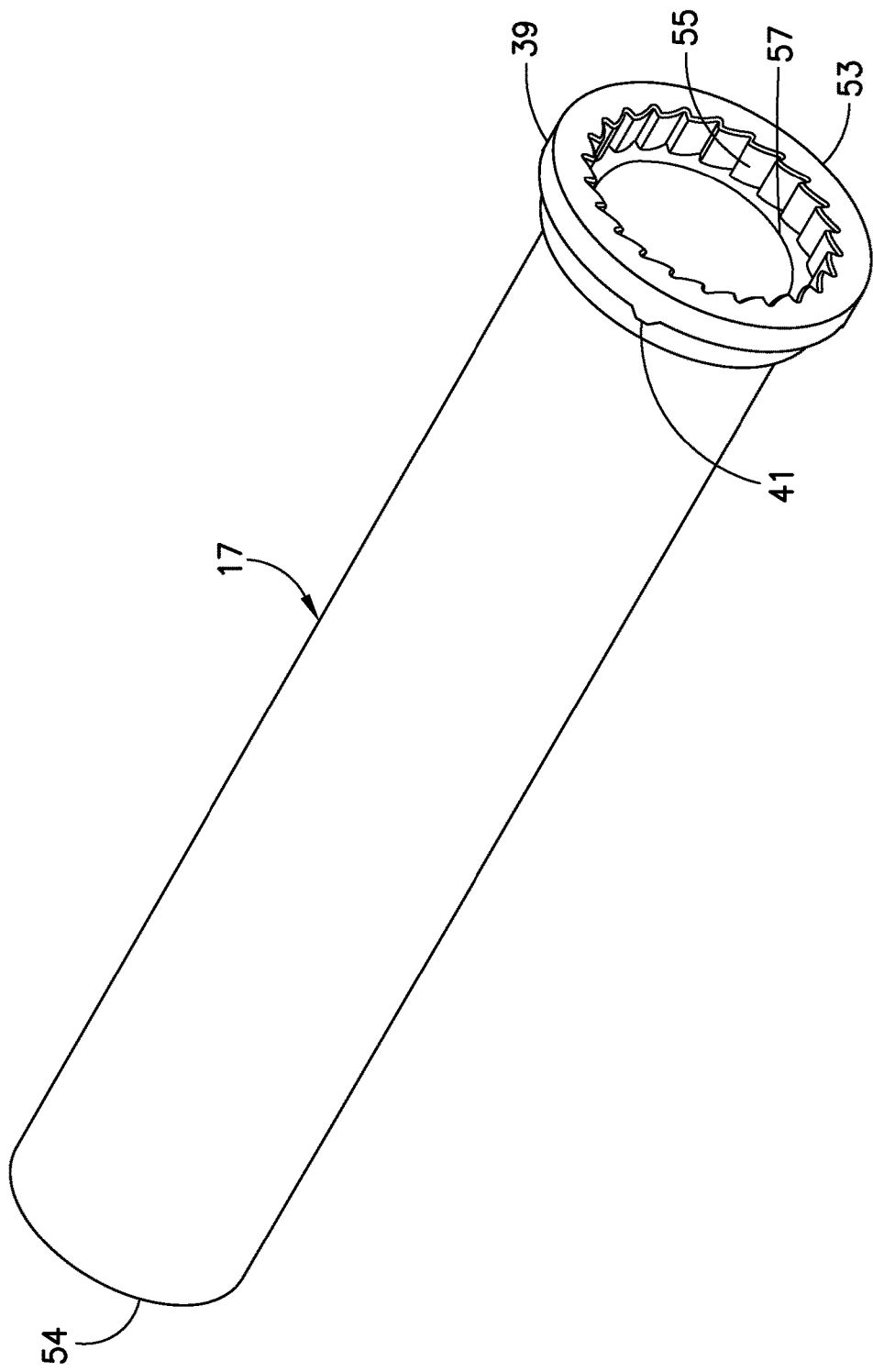
FIG. 21 is a perspective view of a distal end of a setback member of the injection pen of FIG. 7.
Figure 22:
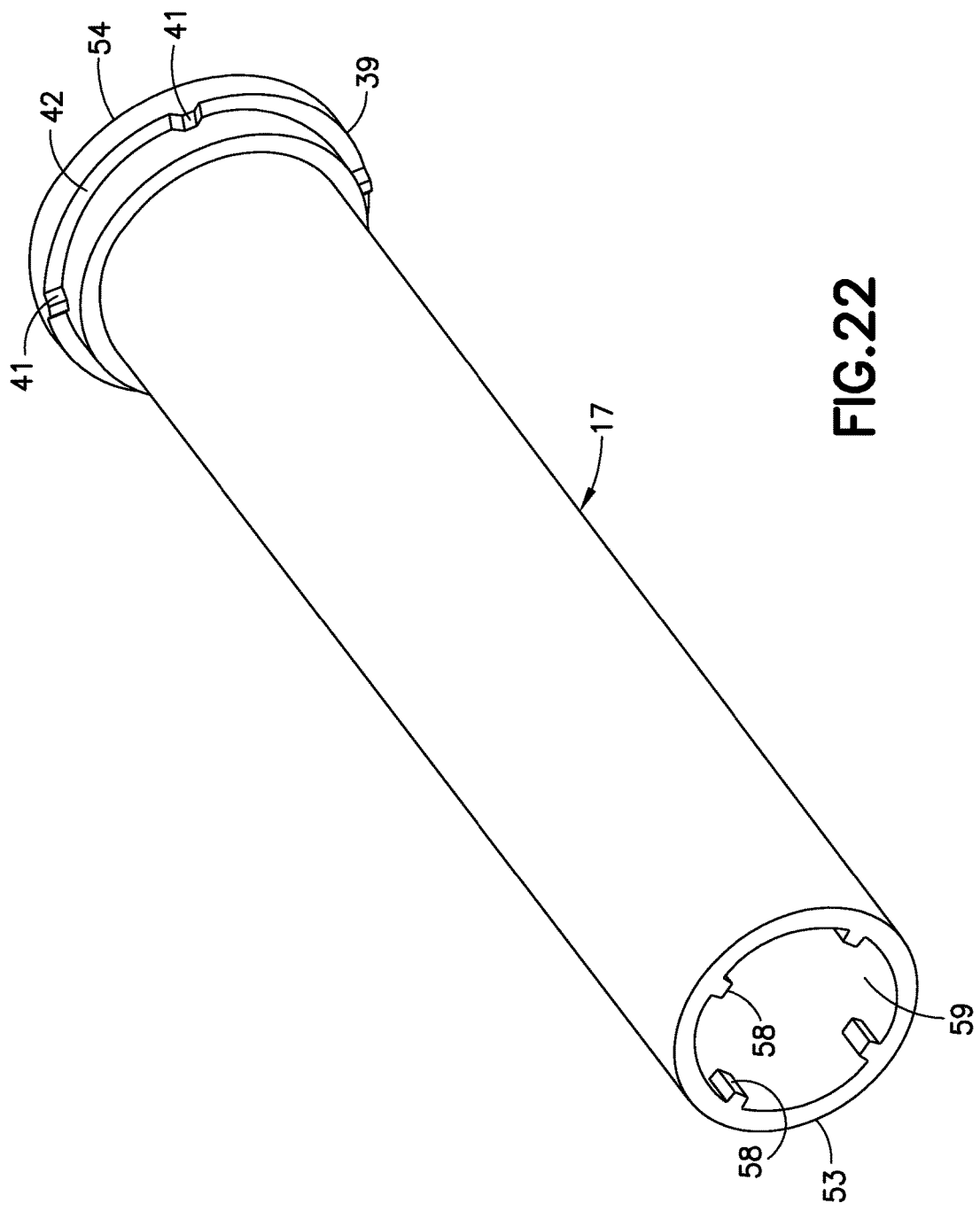
FIG. 22 is a perspective view of a proximal end of the setback member of FIG. 21.

A pair of ratchet arms 31, 32 are formed in the second portion 27 of the upper body 2. The ratchet arms 31, 32 engage a retract nut 33 disposed within the body 2 of the assembled injection pen 1. Ratchet teeth 47, 48 extend inwardly from the ratchet arms 31, 32 respectively. An opening 49 is formed in the interior of the upper body 2, as shown in FIG. 16. A plurality of teeth 50 extend radially inwardly from the opening 49. A thread 51 extends along an inner surface 52 of the body from the first end 24 toward the second end 25. The opening 49 and inwardly extending teeth 50 are disposed between the thread 51 and the ratchet arms 31, 32.

According to an exemplary embodiment shown in FIGS. 17-20, the dose set member 6 is a substantially tubular member having a first end 34 and a second end 35. A thread 36 extends along the outer surface 29 from the second end 35 toward the first end 34, and is received by the internal thread 51 of the upper body 2. The knob portion 37 is disposed at the first end 34. In various exemplary embodiments, an outer surface of the knob portion 37 has gripping features, such as ridges, to facilitate manipulating the dose set member 6. The dose set member 6 includes an annular shoulder or rim 38 on an interior surface 14 thereof, near the first end 34. The annular shoulder 38 engages with an enlarged portion or head 39 of the setback member 17, as shown in FIGS. 4 and 6. The annular shoulder 38 of the dose set member 6 comprises a first mating feature, for example a series of teeth or ridges 40, that engage with a second mating feature, for example one or more similarly shaped teeth or ridges 41, provided on the enlarged head 39 of the setback member 17. The teeth 40 extend longitudinally toward the first end 34 of the dose set member 6, as shown in FIG. 20. A plurality of radially extending ridges or teeth 147 on an inner surface 14 of the knob-like portion 37 are disposed between the annular shoulder 38 and the first end 34.

According to an exemplary embodiment best shown in FIGS. 21-24, the setback member 17 is a substantially tubular member having a first end 53 and a second end 54. The first end 53 includes an enlarged head 39 extending radially outwardly. A plurality of internal teeth or ridges 55 extend radially inwardly from an inner surface 56 of the enlarged head 39. An internal shoulder 57 is formed inwardly of the inner teeth 55, as shown in FIG. 24. One or more teeth 41 extend axially from a surface 42 of the enlarged head 39 of the setback member 17. The second end 54 includes a plurality of radially inwardly extending tabs 58 disposed on an inner surface 59. According to the exemplary embodiment depicted in FIG. 22, the setback member 17 has four tabs 58 evenly spaced, although any suitable number of tabs 58 can be used.

According to an exemplary embodiment shown in FIGS. 25-28, a driver 60 includes a substantially tubular member having a first end 61 and a second end 62. First and second arms 63, 64 extend axially outwardly from the second end 62 of the driver 60. Tabs 73, 74 extend radially outwardly from free ends of the arms 63, 64. First and second ratchet arms 65, 66 extend circumferentially from the first and second arms 63, 64. Hooks 71, 72 extend radially outwardly from free ends of the ratchet arms 65, 66, respectively. Grooves or slots 67 extend axially rearwardly in an outer surface 68 of the driver 60 toward the first end 61. In an exemplary embodiment, the grooves 67 do not extend entirely through to an inner surface 69 of the driver 60, as shown in FIG. 28. The grooves 67 receive the tabs 58 of the setback member 17, such that there are an equal number of grooves 67 and tabs 58. A threaded portion 70 is disposed on the inner surface 69 of the driver 60 at the second end 62, as shown in FIGS. 27 and 28.

Figure 29:
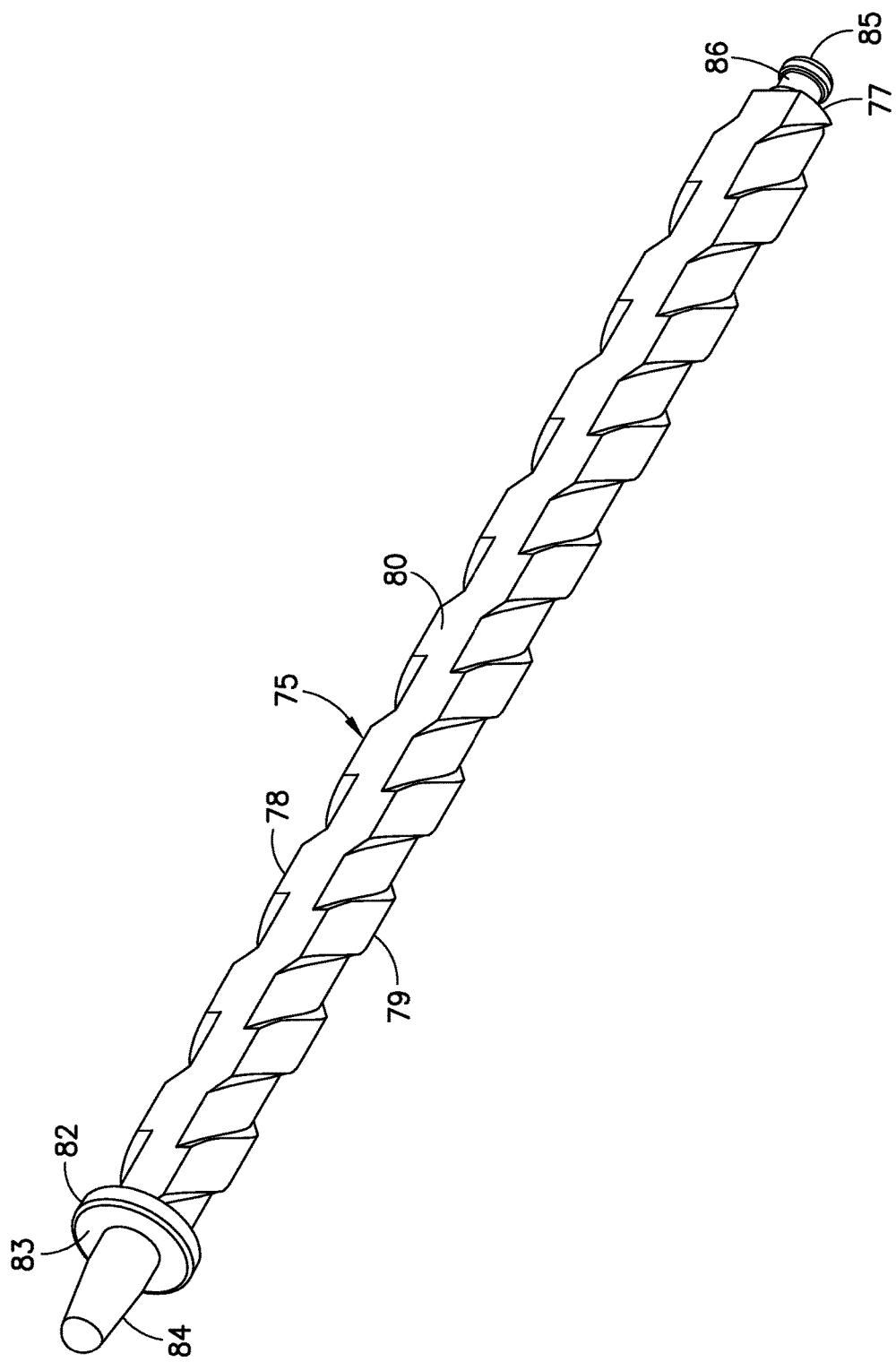
FIG. 29 is a perspective view of a distal end of a lead screw of the injection pen of FIG. 7.
Figure 30:
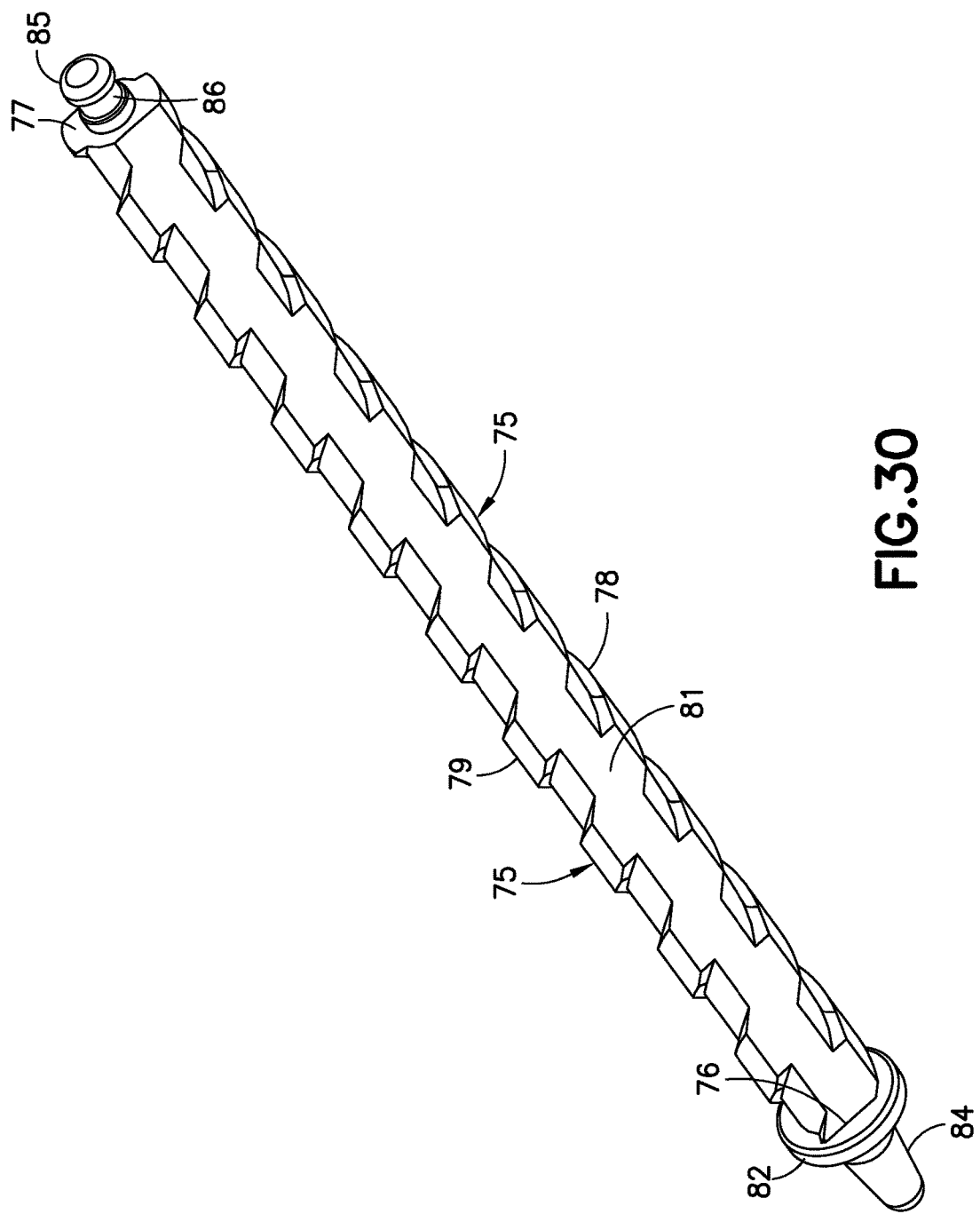
FIG. 30 is a perspective view of a proximal end of a lead screw of FIG. 29.

A lead screw 75 has a first end 76 and a second end 77, as shown in FIGS. 29 and 30. Partial threads 78, 79 are disposed on opposite planar sides 80, 81. A flange 82 is connected to the first end 76 of the lead screw 76 and has a planar surface 83 from which a first protrusion 84 extends axially outwardly. A second protrusion 85 extends axially outwardly from the second end 77 of the lead screw 75. A groove 86 is disposed in the protrusion 85.

Figure 31:
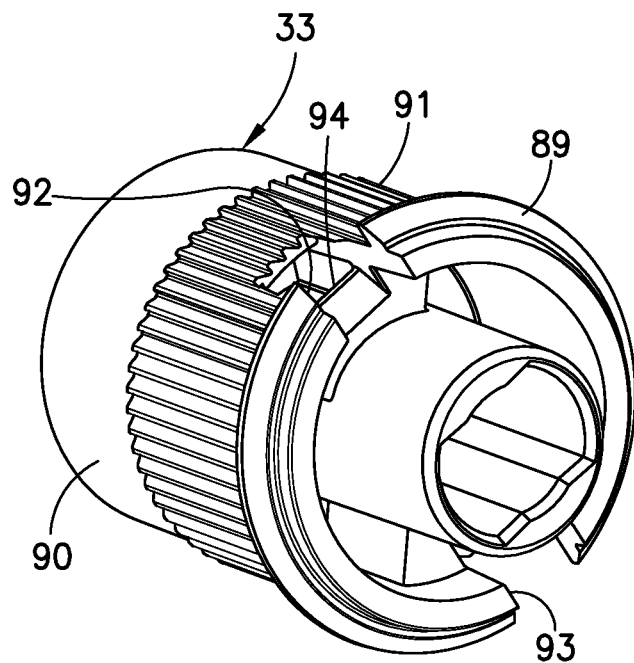
FIG. 31 is a perspective view of a distal end of a retract nut of the injection pen of FIG. 7.
Figure 32:
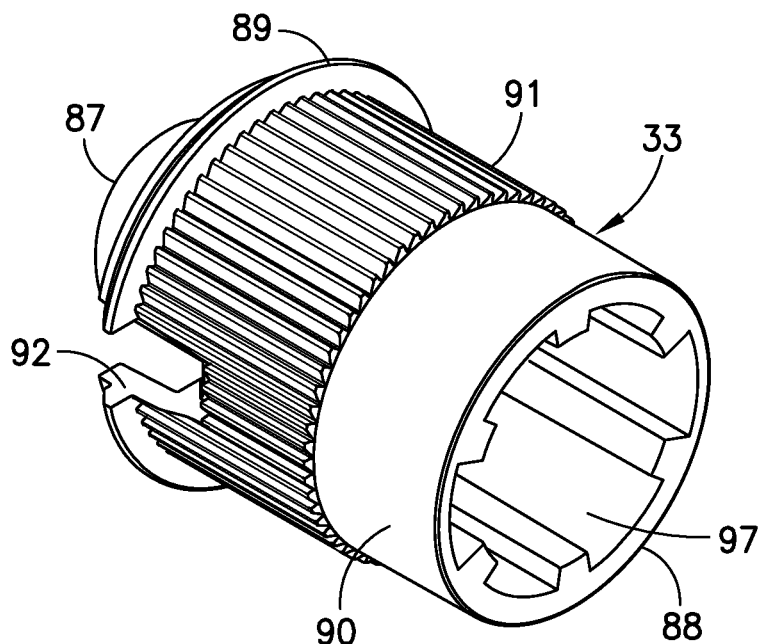
FIG. 32 is a perspective view of a proximal end of the retract nut of FIG. 31.
Figure 33:
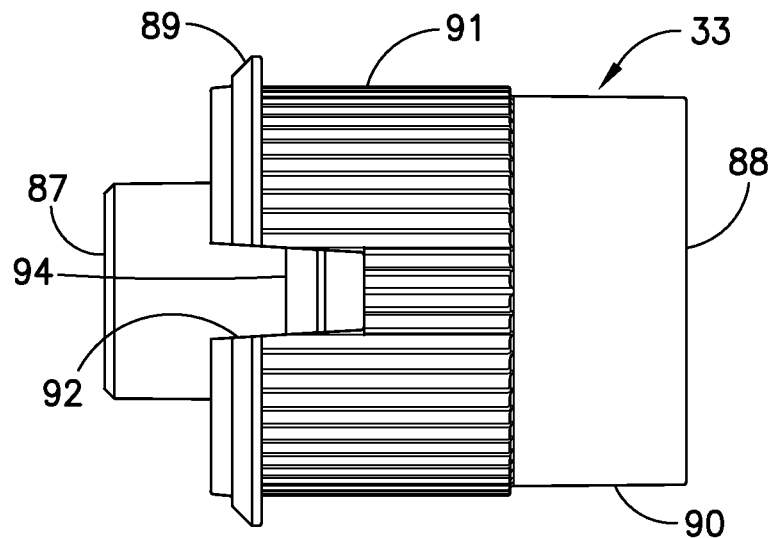
FIG. 33 is a top plan view of the retract nut of FIG. 31.
Figure 34:
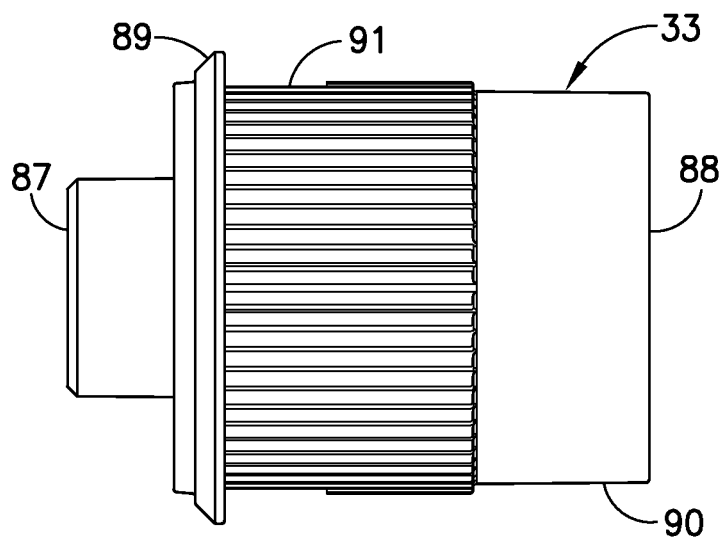
FIG. 34 is a side elevational view of the retract nut of FIG. 31.
Figure 35:
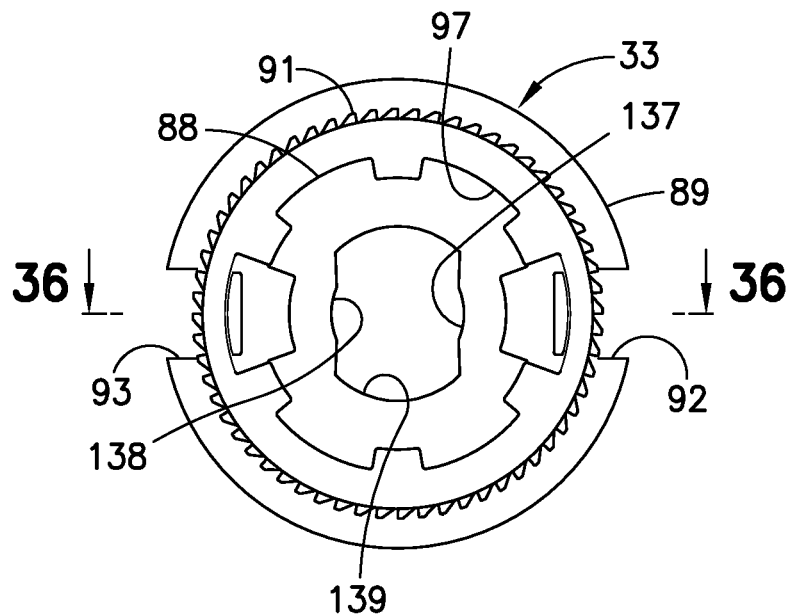
FIG. 35 is a rear elevational view in cross-section of the retract nut of FIG. 31.
Figure 36:
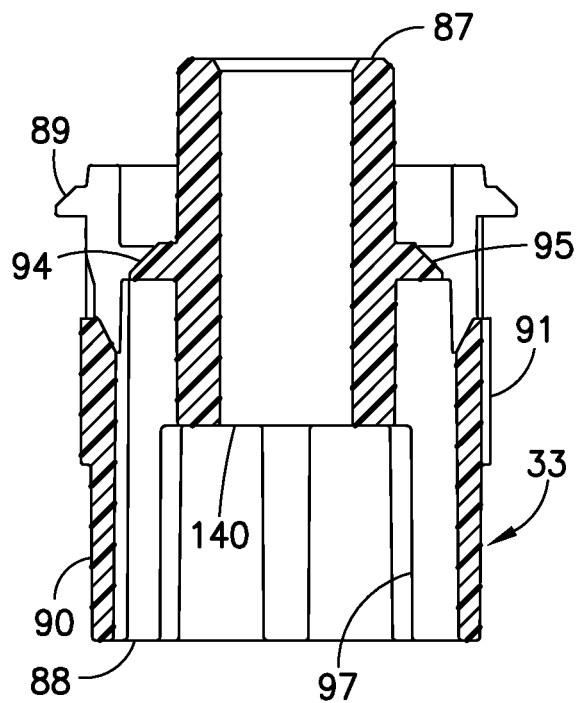
FIG. 36 is a side elevational view in cross-section of the retract nut taken along line 36-36 of FIG. 35.
Figure 37:
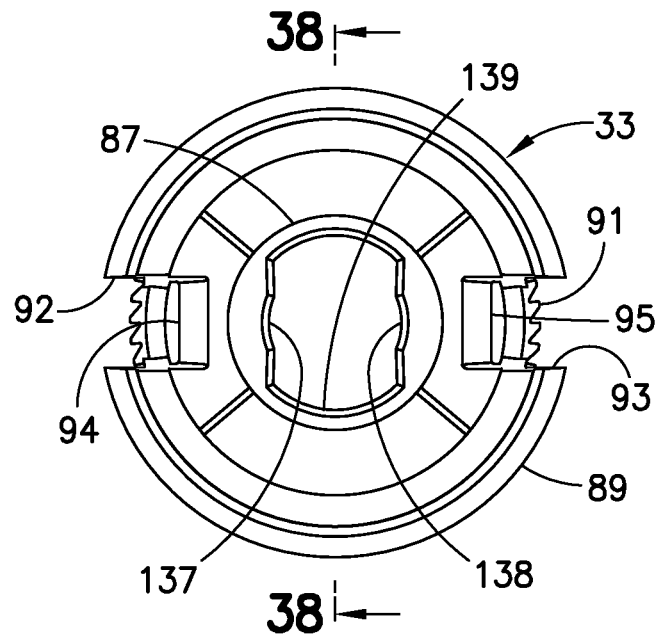
FIG. 37 is a front elevational view in cross-section of the retract nut of FIG. 31.
Figure 38:
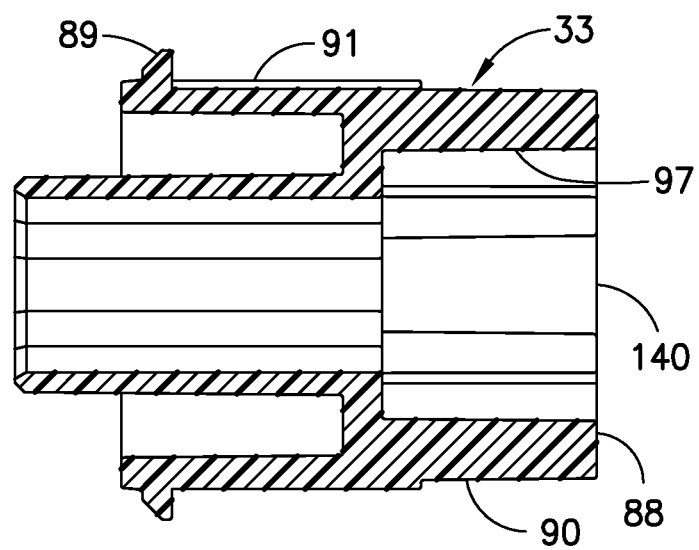
FIG. 38 is a side elevational view in cross-section of the retract nut take along line 38-38 of FIG. 37.
Figure 39:
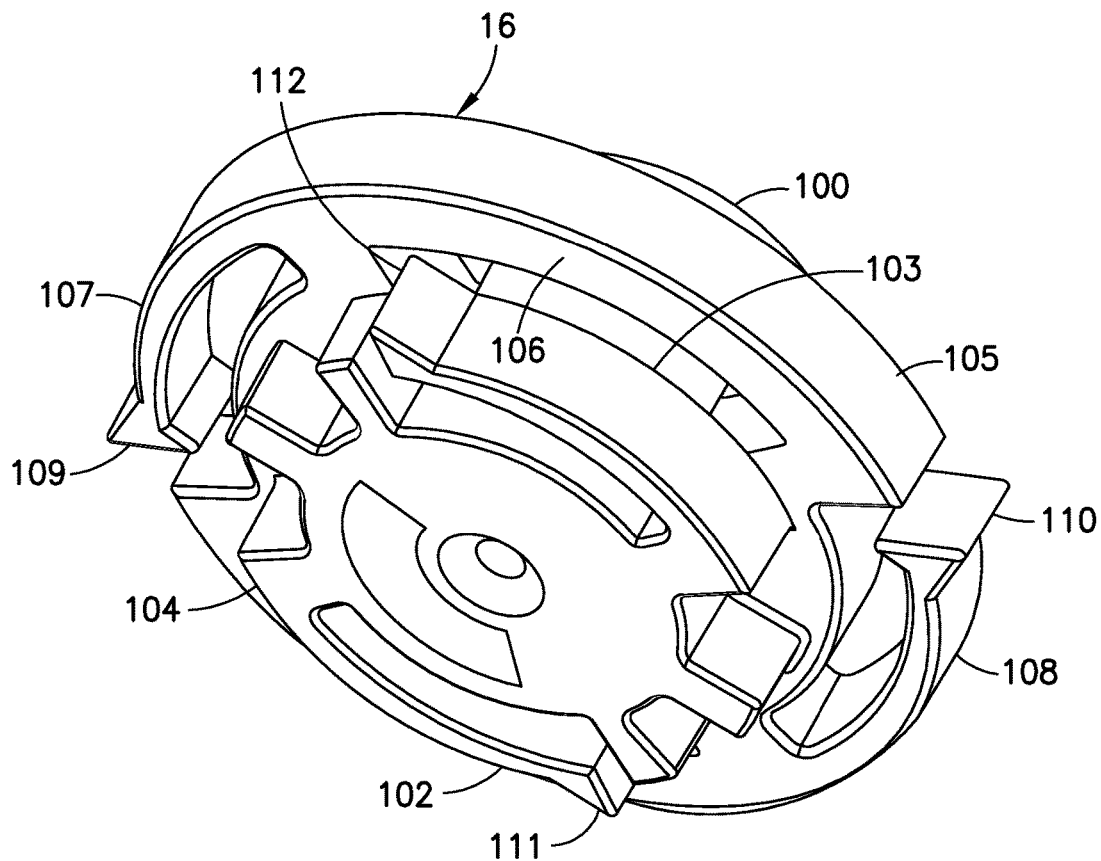
FIG. 39 is a perspective view of a proximal end of a clicker body of the injection pen of FIG. 7.
Figure 40:
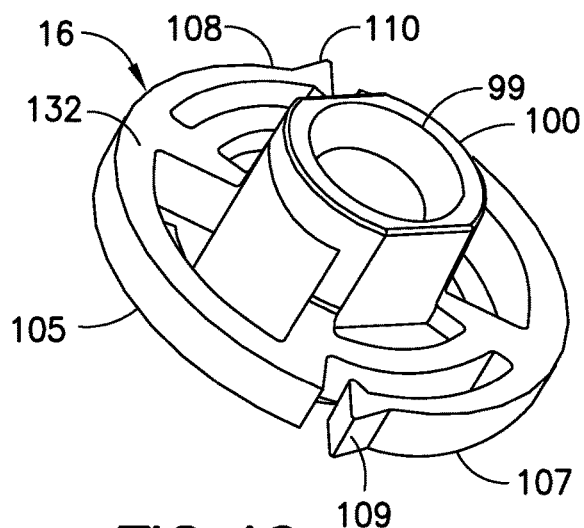
FIG. 40 is a perspective view of a distal end of the clicker body of FIG. 39.
Figure 46:
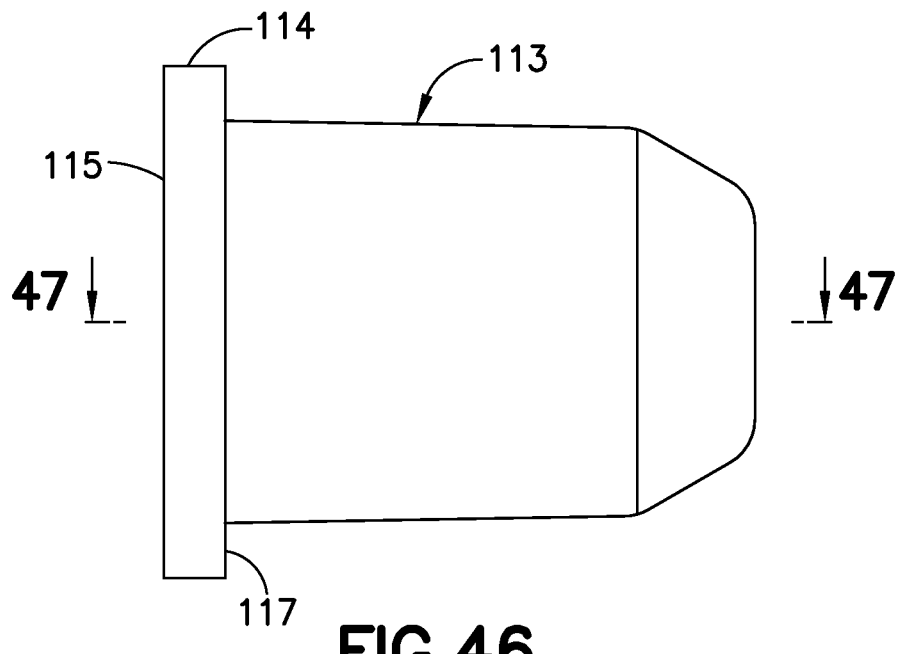
FIG. 46 is a side elevational view of the pilot cap of FIG. 44.
Figure 47:
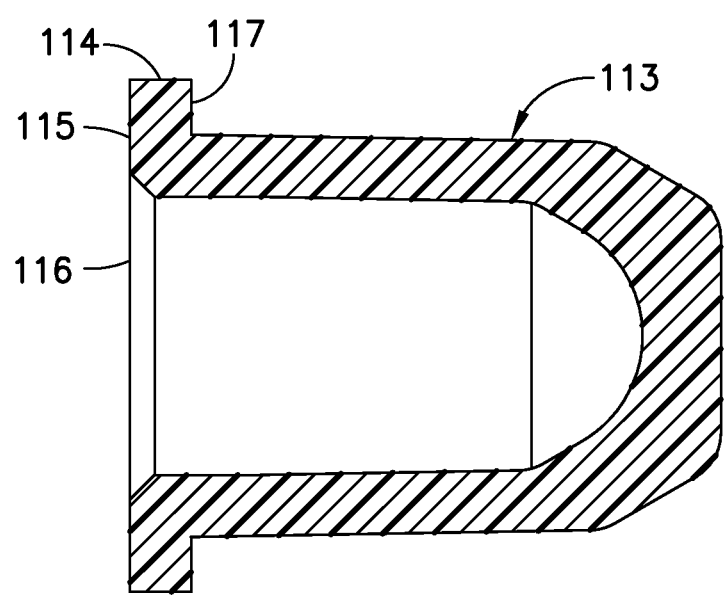
FIG. 47 is a side elevational view in cross-section of the pilot cap taken along line 47-47 of FIG. 46.

According to an exemplary embodiment, the pen 1 utilizes a retract nut 33 having a first end 87 and a second end 88, as shown in FIGS. 7 and 31-38. An annular flange 89 extends outwardly from an outer surface 90 of the retract nut 33 at a first location and a plurality of ridges or teeth 91 extend outwardly from the outer surface 90 at a second location. First and second openings 92, 93 are disposed in the flange 89, as shown in FIGS. 31 and 37. Ramped surfaces 94, 95 are disposed rearwardly of the openings 92, 93 to receive a wave spring 96. A cavity 97 extends inwardly from the second end 88 to receive a spinner 98.

As best shown in FIGS. 39-43, and in accordance with an exemplary embodiment, the clicker body 16 includes a lower ring 104, an upper ring 105 and an opening 99. The upper ring 105 has an outer diameter greater than an outer diameter of the lower ring 104. The clicker body 16 is initially positioned in the dose set member 6 and the opening 99 receives a protrusion 101 of the push button 10. The lower ring 104 includes a lower pair of flexible arms 102, 103 and the upper ring 105 includes an upper pair of flexible arms 107, 108. A lower surface 106 of the upper ring 105 is engaged by the first end 53 of the setback member 17, as shown in FIGS. 4 and 6. Upper hooks 109, 110 are disposed at free ends of the upper flexible arms 107, 108, and lower hooks 111, 112 are disposed at free ends of the lower flexible arms 102, 103. In the exemplary embodiment, the upper hooks 109, 110 and the lower hooks 111, 112 are protrusions having angled or ramped surfaces, although other suitable sizes, shapes, and configurations may be used. The upper hooks 109, 110 engage teeth 40 of the dose set member 6, as shown in FIGS. 4 and 6. The lower hooks 111, 112 engage the teeth 55 of the setback member 17.

According to an exemplary embodiment, a lead screw cap or co-pilot 113, as best shown in FIGS. 44-47, receives the first protrusion 84 of the lead screw 75. A flange 114 is disposed at an end 115 of the co-pilot 113 and has an opening 116 therein for receiving the first protrusion 84 of the lead screw 75. An upper surface 117 of the flange 114 receives a second end 119 of the spring member 15.

Figure 48:
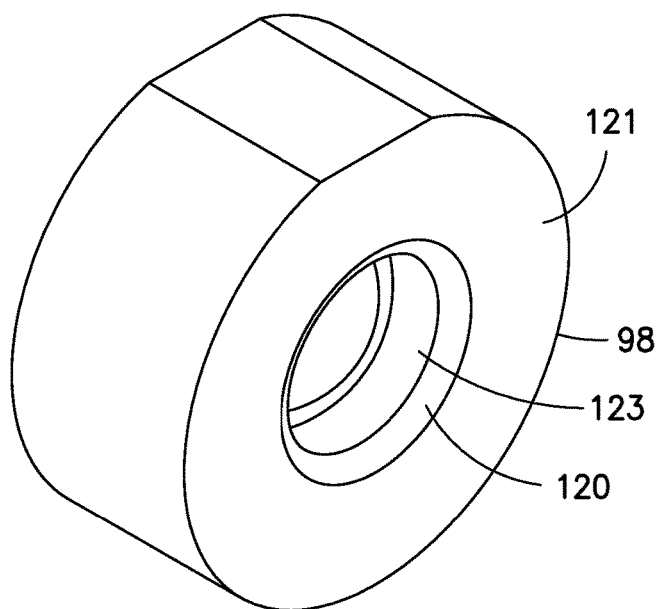
FIG. 48 is a perspective view of a spinner of the injection pen of FIG. 7.
Figure 49:
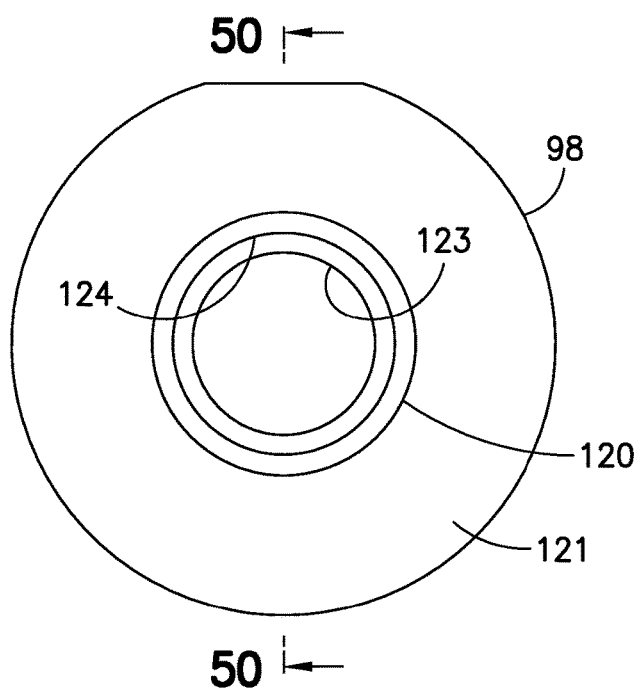
FIG. 49 is a front elevational view of the spinner of FIG. 48.
Figure 50:
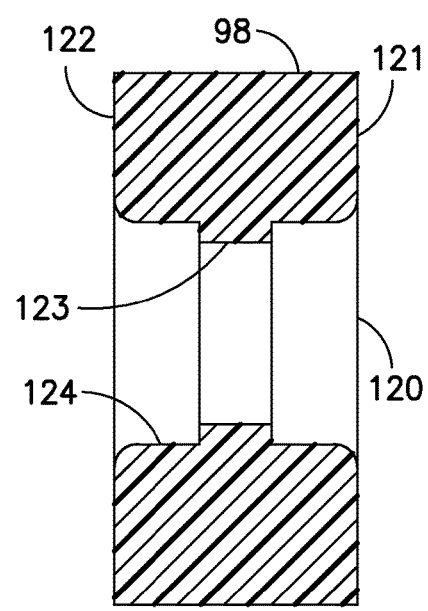
FIG. 50 is a side elevational view in cross-section of the spinner taken along line 50-50 of FIG. 49.

FIGS. 48-50 depict an exemplary spinner 98 that is received by the second protrusion 85 of the lead screw 75. In various exemplary embodiments, the spinner 98 has an opening 120 extending from a first surface 121 to a second surface 122. A rib 123 extends axially outwardly from an inner surface 124 of the opening and is received by the groove 86 in the second protrusion 85 of the lead screw 75. The outer ends of the opening 120 are preferably rounded, as shown in FIG. 50, to facilitate connecting the spinner 98 to the second protrusion 85 of the lead screw 75. The engagement between the rib 123 and the groove 86 substantially prevents axial movement of the spinner 98 with respect to the lead screw 75, and allows rotational movement of the spinner 98 with respect to the lead screw 75.

A spring cap 125 is received within the setback member 17, as shown in FIGS. 4 and 6. In an exemplary embodiment, the spring cap 125 includes a base member 126 having an inner surface 127 engaged by the first end 118 of the spring member 15. A wall 128 extends axially from an outer edge of the base member 126 and has an opening 129 therein to receive the spring member 15. In an exemplary embodiment, the spring member 15 is a helical spring. The first end 118 of the spring member 15 engages the inner surface 127 of the base member 126 of the spring cap 125. The second end 119 engages the upper surface 117 of the flange 114 of the co-pilot 113. The spring member 15 biases the lead screw 75 and spinner 98 in the distal direction to facilitate contact between the lead screw and spinner and the cartridge stopper 44. By maintaining pressure of the lead screw 75 on the stopper 44, accurate administering of the set dose is provided as there is no axial movement of the lead screw 75 before contacting the stopper 44.

The wave spring 96, as shown in FIG. 7, has first and second legs 132 and 133 extending outwardly therefrom. The annular body of the wave spring 96 is substantially wave-shaped. Hooks, such as ramped protrusions, 134 and 135 extend inwardly from free ends of the legs 132 and 133. The wave spring 96 abuts an inner shoulder 136 of the body 2. The hooks 134 and 135 of the legs 132 and 133 of the wave spring 96 engage the ramped surfaces 94 and 95 of the retract nut 33.

Figure 54:
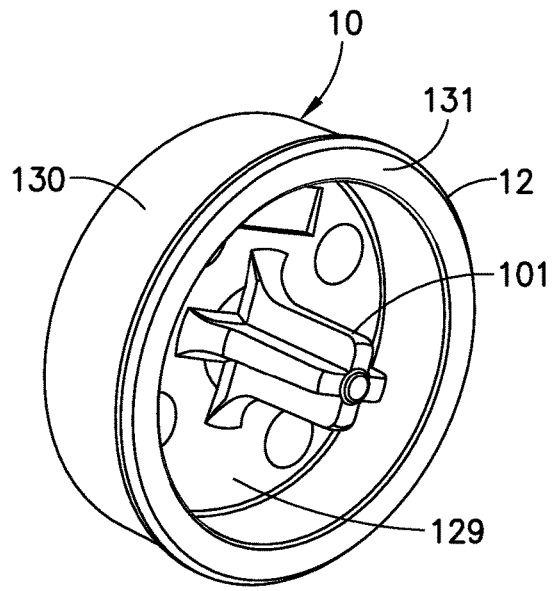
FIG. 54 is a perspective view of a proximal end of a button of the injection pen of FIG. 7.
Figure 55:
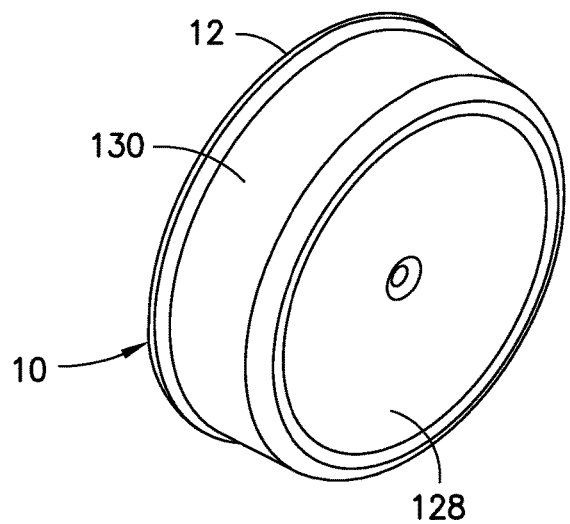
FIG. 55 is a perspective view of an distal end of a button of FIG. 54.
Figure 56:
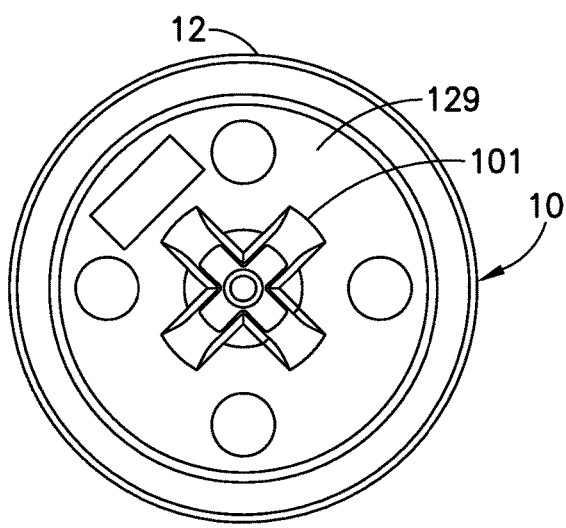
FIG. 56 is a rear elevational view of the button of FIG. 54.

According to an exemplary embodiment, the push button 10, as best shown in FIGS. 54-56, includes a base member 128 having an inner surface 129 from which a protrusion 101 extends axially. A wall 130 extends axially from an outer edge of the base member 128. The annular rim 12 is disposed at a free end of the wall 130. The protrusion 101 is received by the opening 99 in the clicker body 16. A lower surface 131 of the annular rim 12 engages an upper surface 132 of the upper ring 105 during an injection to increase the contact surface area between the push button 10 and the clicker body 16.

Operation and Assembly

The injection pen 1 includes the cap 5 removably attached to a cartridge holder 3 to cover the cartridge holder when the pen is not being used. A pen needle 151 is connected to the threaded portion 11 of the cartridge holder. The pen needle includes a needle having a first end that pierces the septum 45 of the cartridge 4 disposed in the cartridge holder 3 to create a flow path for the medicament stored in the cartridge. The cap 5 covers the needle of the pen needle to substantially prevent accidental needle sticks.

The hooks 134, 135 of the legs 132, 133 of the wave spring 96 are engaged with the ramped surfaces 94, 95 of the retract nut 33. The retract nut 33 is inserted in the second end 25 of the upper body 2 such that the flange 89 is received by the flexible ratchet arms 31, 32. The flange 89 engages the ratchet arms 31, 32 to substantially prevent axial movement of the retract nut 33 in the distal direction out of the upper body 2. The wave spring 96 is disposed between the flange 89 of the retract nut 33 and the shoulder 28 of the upper body 2. The spinner 98 is slid over the second protrusion 85 of the lead screw 75 such that the spinner rib 123 engages the groove 86 in the second protrusion 85, thereby substantially preventing axial movement of the spinner 98 in either axial direction with respect to the lead screw 75. The spinner 98 can move rotationally with respect to the lead screw 75. The second end 77 of the lead screw 75 is passed through the retract nut 33, such that the planar sides 80, 81 are aligned with the planar sides 137, 138 of the opening 139 therein. The retract nut opening 139 substantially prevents rotational movement of the lead screw 75 with respect to the retract nut 33, while allowing axial movement in both directions of the lead screw with respect to the retract nut. The spinner 98 prevents axial movement of the lead screw 75 in the proximal direction when the spinner abuts an inner shoulder 140 of the retract nut, which corresponds to the first or initial position of the lead screw when a new cartridge 4 is inserted in the cartridge holder 3.

The second end 35 of the dose set member 6 is inserted in the first end 24 of the upper body 2 such that the external thread 36 of the dose set member 6 threadably engages the internal thread 51 of the body 2. The threaded connection limits the dose set member 6 to rotational movement with respect to the body. An outer shoulder 141 of the dose set member 6 contacts the first end 24 of the body 2 when the dose set member 6 is fully inserted in the body 2.

The driver 60 is inserted in the setback member 17 such that the internal tabs 58 of the setback member 17 are received by the grooves 67 of the driver 60, thereby rotationally locking the driver 60 to the setback member 17. A second end 62 of the driver 60 is then inserted in the first end 24 of the body 2 such that the internal threads 70 of the driver 60 engage the threads 78 and 79 of the lead screw 75. The driver 60 is then rotated to move the driver axially along the lead screw 75 until the legs 63, 64 pass through the opening 136 in the body 2. The hooks 73, 74 of the legs 63, 64 engage the internal shoulder 136 of the body 2 to substantially prevent axial movement in the proximal direction of the driver 60 with respect to the body 2. The inner surface 56 of the enlarged head 39 of the setback member 17 contacts the inner shoulder 38 of the dose set member 6 to limit axial movement of the setback member 17 in a distal direction.

The co-pilot 113 is disposed on the first protrusion 84 of the lead screw 75 and the second end 119 of the spring member 15 is engaged with the upper surface 117 of the flange 114 of the co-pilot 113. An inner surface 127 of the spring cap 125 is then engaged with the first end 118 of the spring member 15.

The push button protrusion 101 is inserted in the clicker body opening 99. The clicker body 16 is then inserted in the first end 34 of the dose set member 6 such that the annular rim 12 of the push button 10 is received by the annular groove 13 in the dose set member 6.

The cartridge holder 3 is connected to the body 2 such that the internal tabs 21 of the cartridge holder 3 are received by the grooves 30 at the second end 25 of the body 2 to secure the cartridge holder 3 to the body 2. The inner protrusions 23 of the cartridge holder 3 contact and flex inwardly the ratchets arms 31 and 32 of the body 2 when the cartridge holder is connected to the body 2. Ratchet teeth 47 and 48 of the ratchet arms 31 and 32 engage the retract nut teeth 91. Accordingly, the retract nut 33 is substantially prevented from rotational movement when the cartridge holder 3 is connected to the body 2 of the injection pen 1.

Figure 25:
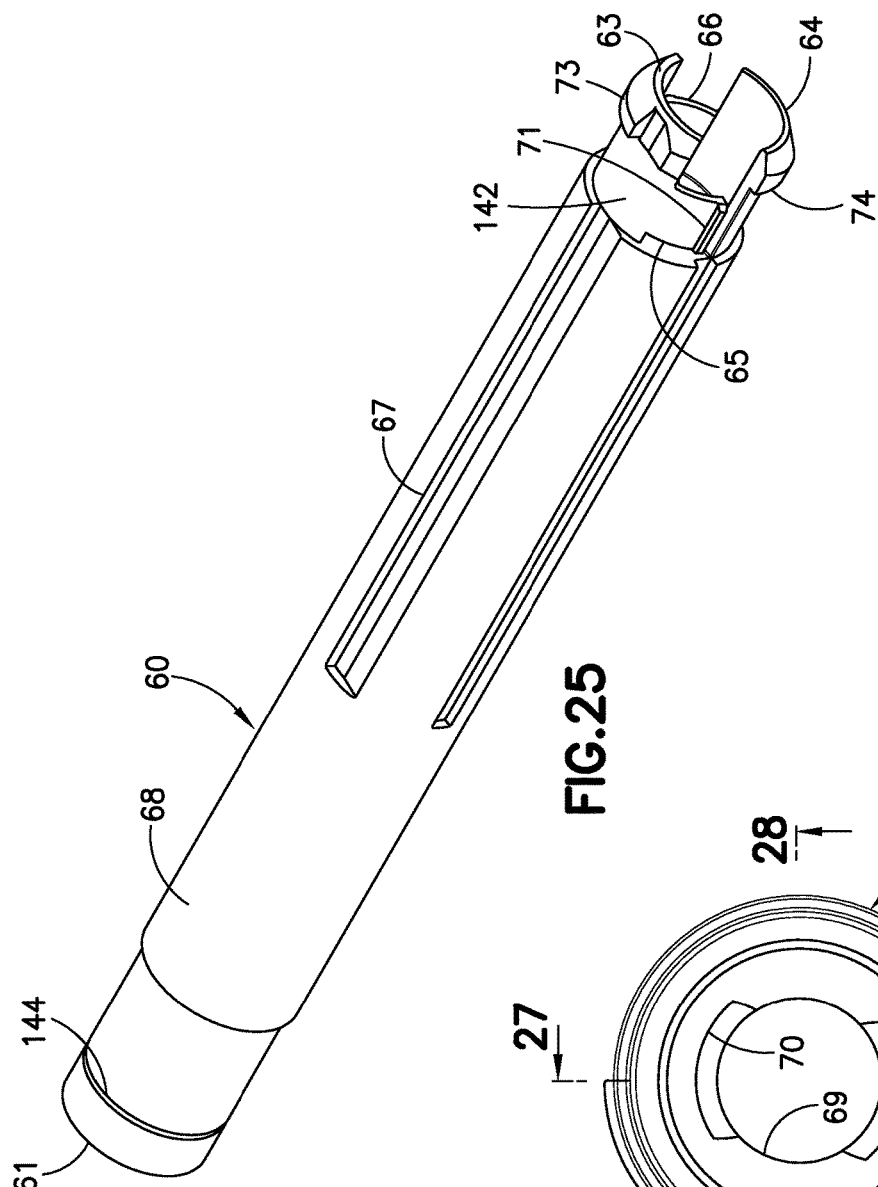
FIG. 25 is a perspective view of a driver of the injection pen of FIG. 7.
Figure 26:
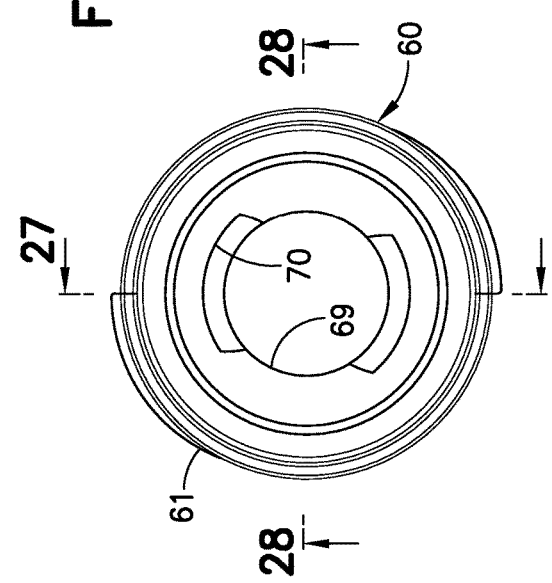
FIG. 26 is a front elevational view of the driver of FIG. 25.

A groove 142, as shown in FIGS. 25, 27 and 28, is formed in the arms 63 and 64 of the driver 60 that is received by inner walls 143 forming the opening 49 in the upper body 2, thereby allowing the driver 60 to rotate, but substantially preventing axial movement of the driver 60 with respect to the body 1. The hooks 71, 72 of the first and second ratchet arms 65, 66 of the driver 60 engage the radially outwardly extending teeth 50 of the body opening 49. The teeth 50 substantially prevent rotation (counter-clockwise) of the driver 60 with respect to the body 2 during dose setting and allow rotation of the driver 60 during injection. The hooks 71, 72 of the ratchets arms 65, 66 create an audible sound, such as a clicking, as the hooks pass over the teeth during injection to indicate to a user that that the injection is occurring.

The flat sides 137, 138 of the retract nut opening 139 mates with the flat sides 80 and 81 of the lead screw 75 to substantially prevent the lead screw 75 from rotating with respect to the retract nut 33. Thus, when the cartridge holder 3 is not connected to the upper body 2, the retract nut 33 and the lead screw 75 are free to rotate. This allows the lead screw 75 to rotatably backdrive into the body 2 against the force of the spring member 15 as the user inserts a new cartridge 4. The lead screw spinner 98 attached to the lead screw 75 rotates freely on the lead screw 75 with respect to the cartridge stopper 44. The spinner 98 increases the contact surface area of the lead screw 75 with the stopper 44, thereby facilitating movement of the stopper through the cartridge 4 by the lead screw 75 during injections.

When the cartridge holder 3 rotationally locks the retract nut 33 within the body 2, the engagement between the flat sides 137 and 138 of the retract nut opening 139 and the flat sides 80 and 81 of the lead screw 75 substantially prevent rotation of the lead screw 75. The internally threaded portion 70 of the driver 60 engages the threaded sides 78 and 79 of the lead screw 75 to drive the lead screw in the distal direction toward and against the cartridge stopper 44 within the cartridge 4 during the injection. Accordingly, during injections, the lead screw 75 does not move rotationally and only moves axially with respect to both the body 2 and the retract nut 33.

The setback member 17 has a plurality of internal tabs 58 therein that travel in corresponding grooves 67 in the driver 60. The axially extending teeth 41 of the setback member 17 engage and lock with the internal teeth 40 on the inner shoulder 38 of the dose set member 6 when the thumb button 10 is pressed during injection.

Figure 57:
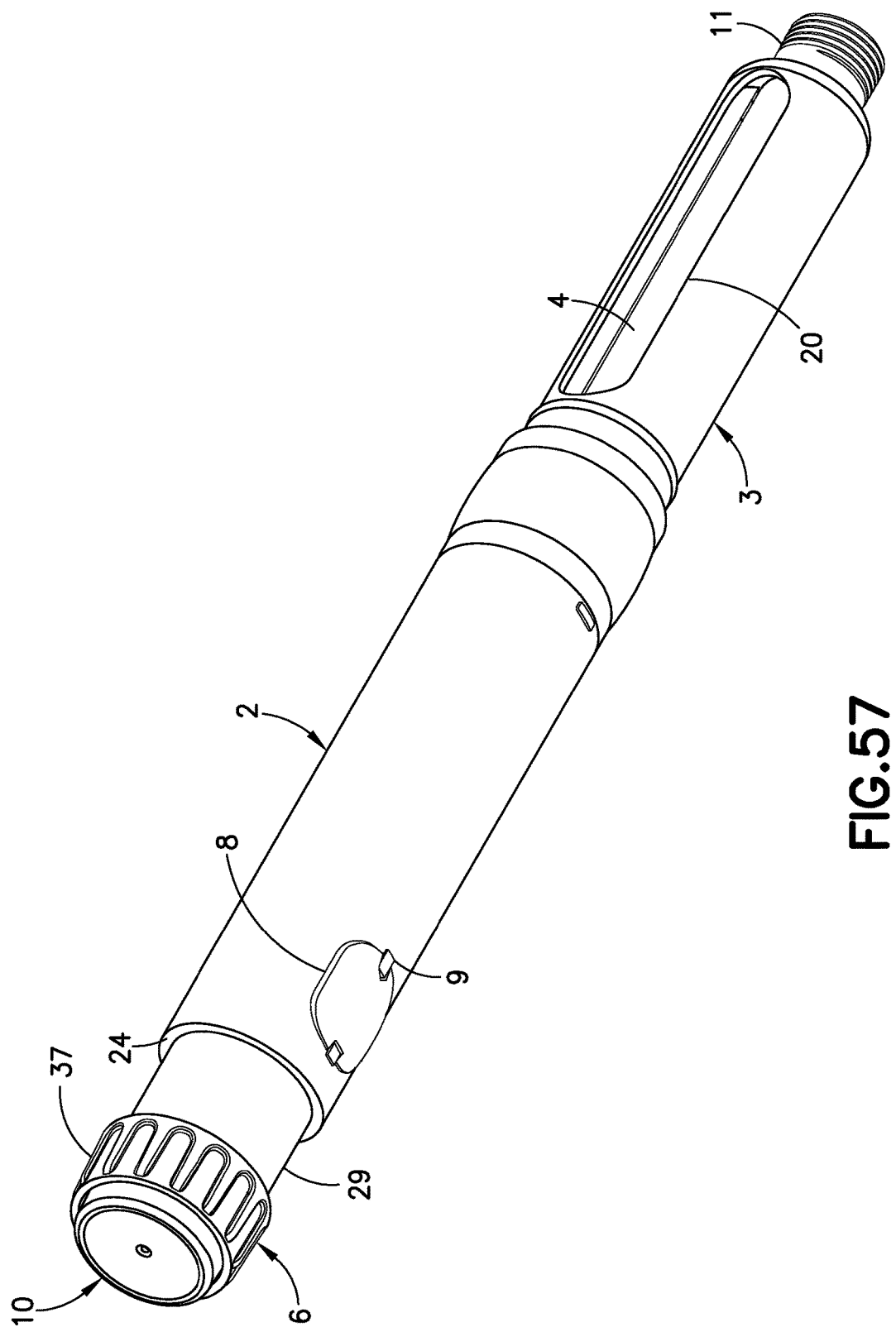
FIG. 57 is a perspective view of the injection pen of FIG. 1 with the dose set member after a dose has been set.

The dose setting thread 51 on the inner surface 52 of the body 2 mates with the external thread 36 of the dose set member 6, enabling the dose set member 6 to rotate out of the body 2 during dose setting, as shown in FIG. 57, and back into the body during the injection. The dose setting number on the outer surface 29 of the dose set member 6 are viewable through the lens 8. The indicator 9 adjacent the lens 8 facilitates properly setting the desired dose.

The thumb button 10 is snapped into the first end 34 of the dose set member 6, allowing relative rotation of the button 10 with respect to the dose set member 6 during the injection. The button 10 also retains the clicker body 16 in engagement with the dose set member 6 and the setback member 17. The upper arms 107, 108 of the clicker body 16 engage the radially extending teeth 147 on the inner surface 14 of the dose set member 6, thereby substantially preventing relative rotation between the dose set member 6 and the clicker body 16 during dial back, but enabling relative rotation in the counter clock-wise direction during dose setting. Accordingly, an audible and/or tactile indication, such as clicking, is generated by the movement of the dose set member 6 relative to the clicker body 16 when setting a dose. The lower arms 102, 103 of the clicker body 16 engage the radially extending teeth 55 on the inner surface 59 of the setback member 17, thereby substantially preventing relative rotation between the setback member 17 and the clicker body 16 during dose setting, but enabling relative rotation in the clockwise direction during dial back. Accordingly, an audible and/or tactile indication, such as clicking, is generated by the movement of the setback member 17 relative to the clicker body 16 when correcting a dose (dial back).

Figure 51:
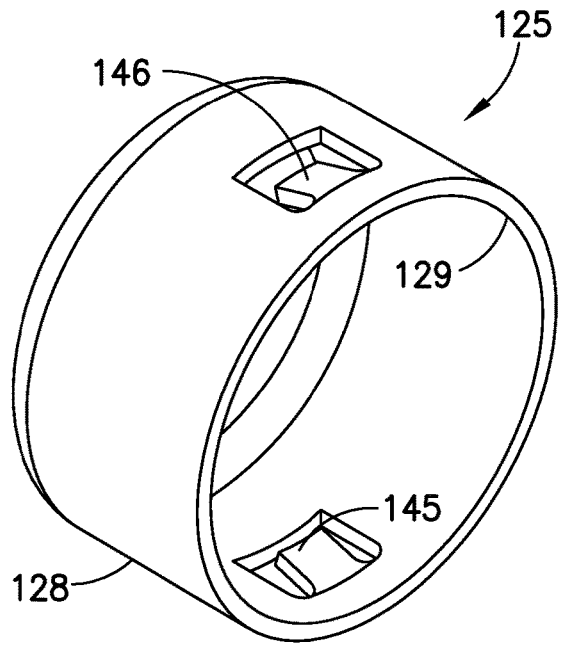
FIG. 51 is a perspective view of a spring cap of the injection pen of FIG. 7.
Figure 52:
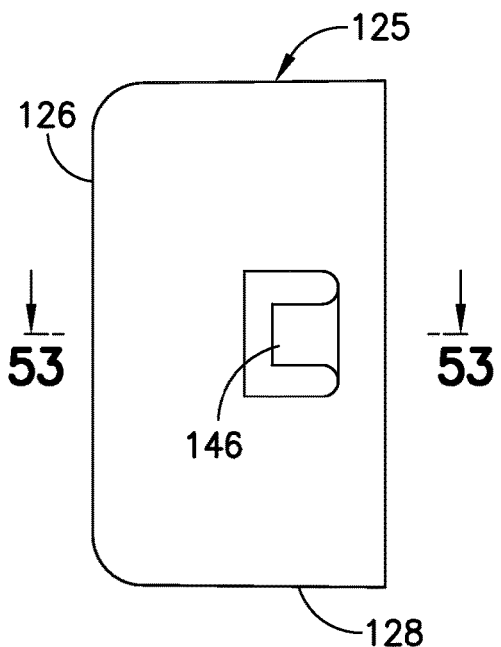
FIG. 52 is a side elevational view of the spring cap of FIG. 51.
Figure 53:
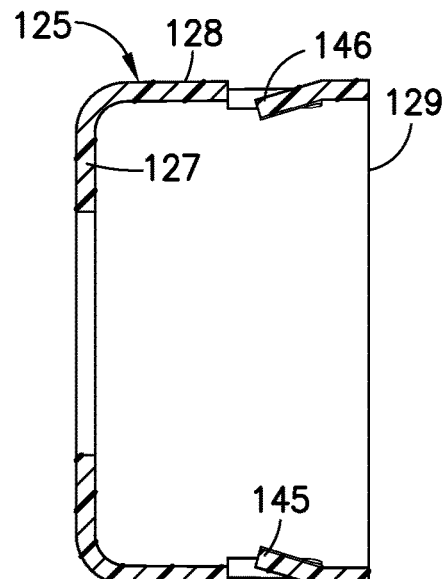
FIG. 53 is a side elevational view in cross-section of the spring cap taken along line 53-53 of FIG. 52.

The spring cap 125 is retained within the setback member 17 on the driver 60 and retains the spring member 15 between the spring cap 125 and the upper surface 117 of the flange 114 of the co-pilot 113. Inwardly extending tabs 145 and 146 (FIGS. 51-53) engage a circumferential groove 144 (FIGS. 25, 27 and 28) of the driver 60 to substantially prevent axial movement of the spring cap 125 in the proximal direction. The spring member 15 biases the lead screw 75 in the distal direction so that the lead screw 75 substantially maintains contact with the cartridge stopper 4, particularly after replacing an old cartridge with a new cartridge. The wave spring 96 biases the retract nut 33 in the distal direction, such that the second end 88 of the retract nut 33 abuts an end 148 of the cartridge 4, as shown in FIGS. 4 and 6. The biasing force of the wave spring 96 substantially prevents movement of the cartridge 4, such as rattling, when disposed in the cartridge holder 3.

To set a dose, the user rotates the dose set member 6 in a clockwise direction until the desired dose is displayed in the dose display lens 8 in the upper body 2. The plurality of dosage numerals on the outer surface of the dose set member 6 are visible through the lens 8. When the desired dose is reached, the user depresses the thumb button 10 to inject the dose until the dose set member 6 has fully returned into the body 2.

During dose setting, the dose set member 6 rotates outwardly and away from the first end 24 of the upper body 2, as shown in FIG. 57. The internal shoulder 38 of the dose set member 6 contacts the surface 42 of the enlarged head portion 39 of the setback member 17 and drags the setback member 17 axially in the proximal direction with the dose setting member 6. The inner tabs 58 of the setback member 17 move axially in the grooves 67 of the driver 60, which remains rotationally and axially fixed. The engagement between the setback member tabs 58 and the driver grooves 67 substantially prevents rotational movement of the setback member 17 with respect to the driver 60. Also during dose setting, the clutch teeth 41 on the enlarged head portion 39 of the setback member 17 slide over the teeth 40 of the dose set member 6 because there is not enough axial pressure to lock the setback teeth 41 with the dose set member teeth 40. As the dose set member 6 rotates away from the upper body 2, the clicker body 16 upper pair of arms 107, 108 pass over the teeth 147 of the dose set member 6, thereby generating an audible and/or tactile indication. The lower pair of arms 102, 103 remain locked with the teeth 55 of the setback member 17.

During both dose setting and dose correcting (dial back), the setback member 17 is substantially prevented from rotational movement. Accordingly, the driver 60 is also substantially prevented from rotational movement. Axial movement of the lead screw 75 is also substantially prevented because the driver 60 is prevented from rotating during dose setting and correcting.

When the user overshoots the desired dose, the dose set member 6 can be dialed back, for example counter-clockwise, to the desired correct dose. The dose set member 6 is rotated in the opposite direction from the dose setting direction, for example clockwise, back into the upper body 2 until the desired dose is displayed in the lens 8. The dose set member 6 is freely rotatable back into the upper body 2 to correct the set dose without performing additional steps or functions. During dose correcting, the setback member 17 is locked against rotation by the engagement of the setback member tabs 58 with the driver grooves 67. The axial pressure exerted during dial back is insufficient to engage the clutch teeth 41 of the setback member 17 with the teeth 40 of the dose set member 6. As the dose set member 6 rotates back into the body 2, the lower arms 102, 103 of the clicker body 16 pass over the teeth 55 of the setback member 17, thereby providing an audible and/or tactile indication of the dial back. The upper arms 107, 108 remain locked with the teeth 147 of the dose set member 6.

During injection, the user depresses the thumb button 10 until the dose set member 6 fully rotates back into the upper body 2. As the dose set member 6 rotates back into the upper body 2, the clutch teeth 41 of the setback member 17 lock with the teeth 40 on the dose set member 6 such that the dose set member 6 and the setback member 17 rotate together. The rotation of the setback member 17 causes the driver 60 to rotate as the setback member travels down the driver 60 in the distal direction due to the engagement of the setback member tabs 58 in the driver grooves 67. As the driver 60 rotates, the inner threads 70 of the driver 60 drive the lead screw 75 in the distal direction, thereby pushing the stopper 44 axially through the cartridge 4 and injecting the medication. The lead screw 75 does not rotate during injection because it is keyed to the flat sides 137, 138 of the retract nut 33, which is rotationally fixed to the upper body 2 while the cartridge holder 3 is connected to the upper body 2. As the driver 60 rotates, the hooks 71, 72 of the first and second ratchets arms 65, 66 of the driver 60 pass over the radially outwardly extending teeth 50 of the body opening 49 of the upper body 2, thereby generating an audible and/or tactile indication during injection of a dose.

To replace a cartridge, the user unscrews or disengages the cartridge holder 3 from the upper body 2 and removes the old cartridge. A new cartridge is disposed in the cartridge holder 3. As the cartridge holder 3 is reattached to the upper body 2, the stopper 44 of the cartridge exerts pressure on the spinner 98. The ratchet arms 31, 32 do not prevent rotation of the retract nut 33 because the protrusions 23 of the cartridge holder 3 have not yet engaged the ratchet arms 31, 32 of the upper body 2, such that the retract nut 33 is free to rotate. The driver 60 is axially and rotationally locked to the upper body 2. The force exerted by the cartridge stopper 44 on the spinner 98 and lead screw 75 causes the lead screw 75 to rotate through the internal threads 70 of the driver 60. The spinner 98 is free to rotate on the lead screw 75 such that undue pressure is not exerted on the stopper 44. The ratchet arms 31, 32 of the upper body 2 passing over the teeth 91 of the retract nut 33 generate an audible and/or tactile indication that the lead screw 75 is being backdriven into the body. When the cartridge holder protrusions 23 engage the body ratchet arms 31, 32, the ratchet arms 31, 32 are flexed inwardly to engage teeth 91 of the retract nut 33 to stop rotation of the retract nut 33. Once the retract nut 33 stops rotating, the lead screw 75 is prevented from further rotation by the engagement of the flat sides 137 and 138 of the retract nut opening 139 with the flat sides 80 and 81 of the lead screw 75.

The foregoing detailed description of the certain exemplary embodiments has been provided for the purpose of explaining the principles of the invention and its practical application, thereby enabling others skilled in the art to understand the invention for various embodiments and with various modifications as are suited to the particular use contemplated. This description is not necessarily intended to be exhaustive or to limit the invention to the exemplary embodiments disclosed. Any of the embodiments and/or elements disclosed herein may be combined with one another to form various additional embodiments not specifically disclosed. Accordingly, additional embodiments are possible and are intended to be encompassed within this specification and the scope of the appended claims. The specification describes specific examples to accomplish a more general goal that may be accomplished in another way.

As used in this application, the terms "front," "rear," "upper," "lower," "upwardly," "downwardly," and other orientational descriptors are intended to facilitate the description of the exemplary embodiments of the present invention, and are not intended to limit the structure of the exemplary embodiments of the present invention to any particular position or orientation. Terms of degree, such as "substantially" or "approximately" are understood by those of ordinary skill to refer to reasonable ranges outside of the given value, for example, general tolerances associated with manufacturing, assembly, and use of the described embodiments.

The invention claimed is:

1. An injection pen, comprising:
    a housing;
    a lead screw axially moveable in the housing and decoupled from the housing to provide free rotation therebetween;
    a dose set member for dose setting and dose correcting and connected to the housing;
    a setback member operatively connected to the dose set member;
    a clicker operatively coupled to the dose set member and the setback member, the clicker positioned in the dose set member; and
    a rotatable driver operatively connected to the setback member and the lead screw,
    wherein the driver is prevented from rotating during dose setting and dose correcting, and the driver rotates during an injection to axially move the lead screw.

2. The injection pen of claim 1, wherein the clicker includes an upper ring having an upper arm and a lower ring having a lower arm.

3. The injection pen of claim 2, wherein the upper arm engages the dose set member and the lower arm engages the setback member.

4. The injection pen of claim 2, wherein the lower arm prevents relative rotation between the clicker and the setback member during dose setting and the upper arm prevents relative rotation between the clicker and the dose set member during dose correcting.

5. The injection pen of claim 2, wherein the upper ring has an outer diameter greater than an outer diameter of the lower ring.

6. The injection pen claim 2, wherein the upper arm creates an audible signal during dose setting and the lower arm creates an audible signal during dose correcting.

7. The injection pen of claim 2, wherein the upper arm engages one or more teeth on the dose set member and the lower arm engages one or more teeth on the setback member.

8. The injection pen of claim 1, further comprising a push button connected to the clicker.

9. The injection pen of claim 1, further comprising a cartridge bolder releasably connected to the housing and a retract nut operatively connected to the housing and the lead screw.

10. The injection pen of claim 9, wherein the lead, screw rotates with respect to the retract nut when the cartridge holder is disconnected from the housing.

11. The injection pen of claim 9, wherein the lead screw is rotationally fixed to the retract nut when the cartridge holder is connected to the housing.

12. The injection pen of claim 11, wherein the housing comprises a ratchet arm biased into engagement with the retract nut by the cartridge holder.

13. The injection pen of claim 9, further comprising a spring biasing the retract nut in a distal direction.

14. The injection pen of claim 1, wherein the dose set member is rotated out of the housing in a first direction to set a dose, and the dose set member is freely rotatable in a second direction to correct a set dose.

15. An injection pen, comprising:
    a housing;
    a lead screw axially moveable in the housing;
    a dose set member for dose setting and dose correcting and connected to the housing;
    a setback member operatively connected to the dose set member; and
    a rotatable driver operatively connected to the setback member and the lead screw,
    wherein the driver is prevented from rotating during dose setting and dose correcting, and the driver rotates during an injection to axially move the lead screw;
    wherein the dose set member is rotated out of the housing in a first direction to set a dose, rotated into the housing in a second direction to correct a dose, and rotated into the housing in the second direction during injection;
    wherein the lead screw does not rotate during injection; and
    wherein the setback member is axially moveable with respect to the driver.

16. The injection pen of claim 15, wherein the setback member moves axially with the dose set member without rotation therebetween, with respect to the housing during dose setting and dose correcting, and rotates with the dose set member during injection.

17. The injection pen of claim 15, wherein the driver is rotationally locked to the setback member.

18. The injection pen of claim 15, wherein the setback member mates with the dose set member to rotationally lock the setback member and the dose set member during injection.

19. An injection pen, comprising:
    a housing;
    a lead screw axially moveable in the housing;
    a dose set member for dose setting and dose correcting and connected to the housing;
    a setback member operatively connected to the dose set member; and
    a rotatable driver operatively connected to the setback member and the lead screw, wherein the driver is prevented from rotating during dose setting and dose correcting, and the driver rotates during an injection to axially move the lead screw;

wherein the dose set member is rotated out of the housing in a first direction to set a dose, rotated into the housing in a second direction to correct a dose, and rotated into the housing in the second direction during injection;

wherein the lead screw does not rotate during injection; and wherein the dose set member includes a set of first teeth, and the setback member includes at least one second tooth mating with the first teeth during injection.

20. The injection pen of claim 15, further comprising a push button and a clicker connected to the dose set member.

21. An injection pen, comprising:
a housing;
a lead screw axially moveable in the housing;
a dose set member for dose setting and dose correcting and connected to the housing;
a setback member operatively connected to the dose set member;
a rotatable driver operatively connected to the setback member and the lead screw; and
a push button and a clicker connected to the dose set member,
wherein the driver is prevented from rotating during dose setting and dose correcting, and the driver rotates during an injection to axially move the lead screw;
wherein the dose set member is rotated out of the housing in a first direction to set a dose, rotated into the housing in a second direction to correct a dose, and rotated into the housing in the second direction during injection;
wherein the lead screw does not rotate during injection; and
wherein a force applied to the push button during injection causes the setback member to engage the dose set member.

22. The injection pen of claim 15, further comprising a cartridge holder releasably connected to the housing, and a retract nut operatively connected to the housing and the lead screw, wherein the lead screw rotates with respect to the retract nut when the cartridge holder is disconnected from the housing and the lead screw is rotationally fixed to the retract nut when the cartridge holder is connected to the housing.

23. An injection pen, comprising:
a housing;
a lead screw axially moveable in the housing;
a dose set member for dose setting and dose correcting, threadably connected to the housing and having a first mating feature;
a setback member having a second mating feature for engaging the first mating feature;
a clicker operatively connected to the dose set member;
a push button operatively connected to the setback member to cause the second mating feature to engage the first mating feature during an injection, the push button receiving the clicker; and
a cartridge holder and a retract nut connected to the housing and receiving the lead screw;
wherein the first mating feature is disengaged from the second mating feature during dose setting and dose correcting and engaged with the second mating feature during an injection; and
wherein the lead screw rotates with respect to the retract nut when the cartridge holder is disconnected from the housing and the lead screw is rotationally fixed to the retract nut when the cartridge holder is connected to the housing.

* * * * *